(12) United States Patent
Diederich et al.

(10) Patent No.: US 10,232,195 B2
(45) Date of Patent: Mar. 19, 2019

(54) APPARATUS AND METHODS FOR TRANSURETHRAL TREATMENT OF STRESS URINARY INCONTINENCE

(71) Applicants: THE REGENTS OF THE UNIVERSITY OF CALIFORNIA, Oakland, CA (US); ACOUSTIC MEDSYSTEMS, INC., Savoy, IL (US)

(72) Inventors: Chris J. Diederich, Novato, CA (US); Everette C. Burdette, Champaign, IL (US); Jeffery H. Wootton, San Francisco, CA (US)

(73) Assignee: ACOUSTIC MEDSYSTEMS, INC., Savoy, IL (US)

( * ) Notice: Subject to any disclaimer, the term of this patent is extended or adjusted under 35 U.S.C. 154(b) by 559 days.

(21) Appl. No.: 14/567,559

(22) Filed: Dec. 11, 2014

(65) Prior Publication Data
US 2015/0202467 A1    Jul. 23, 2015

Related U.S. Application Data

(63) Continuation of application No. PCT/US2013/048350, filed on Jun. 27, 2013.
(Continued)

(51) Int. Cl.
*A61N 7/00* (2006.01)
*A61N 7/02* (2006.01)
(Continued)

(52) U.S. Cl.
CPC ............... *A61N 7/00* (2013.01); *A61N 7/022* (2013.01); *A61B 2017/00805* (2013.01);
(Continued)

(58) Field of Classification Search
CPC ........... A61B 2017/00805; A61B 2018/00023; A61B 2018/00285; A61B 2018/00523; A61F 2007/005; A61N 7/00; A61N 7/022
See application file for complete search history.

(56) References Cited

U.S. PATENT DOCUMENTS 6,081,749 A    6/2000  Ingle
2002/0193781 A1  12/2002  Loeb
(Continued)

FOREIGN PATENT DOCUMENTS

WO    2003059437 A2    7/2003
WO    2004010843 A2    2/2004

OTHER PUBLICATIONS

Korean Intellectual Property Office (KIPO), International Search Report and Written Opinion dated Oct. 16, 2013, counterpart PCT international application No. PCT/US2013/048350, pp. 1-14, with claims searched, pp. 15-20.

*Primary Examiner* — Michael T Rozanski
(74) *Attorney, Agent, or Firm* — O'Banion & Ritchey LLP; John P. O'Banion

(57) ABSTRACT

Transurethral ultrasound treatment system and methods that provide targeted treatment zones outside urethra via an applicator with multiple sectors, a urethral cooling balloon, and bladder positioning balloon for directed application in muscle tissue. In one embodiment, the system and methods are configured to generate thermal lesions via simultaneous sonication or activation of two separate sectors from a tubular device, with an inactive zone directed toward vaginal wall or nerves.

23 Claims, 34 Drawing Sheets

Related U.S. Application Data

(60) Provisional application No. 61/665,299, filed on Jun. 27, 2012.

(51) Int. Cl.
*A61B 17/00* (2006.01)
*A61B 18/00* (2006.01)
*A61F 7/00* (2006.01)

(52) U.S. Cl.
CPC .............. *A61B 2018/00023* (2013.01); *A61B 2018/00285* (2013.01); *A61B 2018/00523* (2013.01); *A61F 2007/005* (2013.01)

(56) References Cited

U.S. PATENT DOCUMENTS

| | | | |
|---|---|---|---|
| 2003/0178032 A1* | 9/2003 | Ingle | A61B 18/1485 128/898 |
| 2009/0281463 A1 | 11/2009 | Chapelon | |
| 2013/0131668 A1* | 5/2013 | Schaer | A61B 8/4281 606/41 |

* cited by examiner

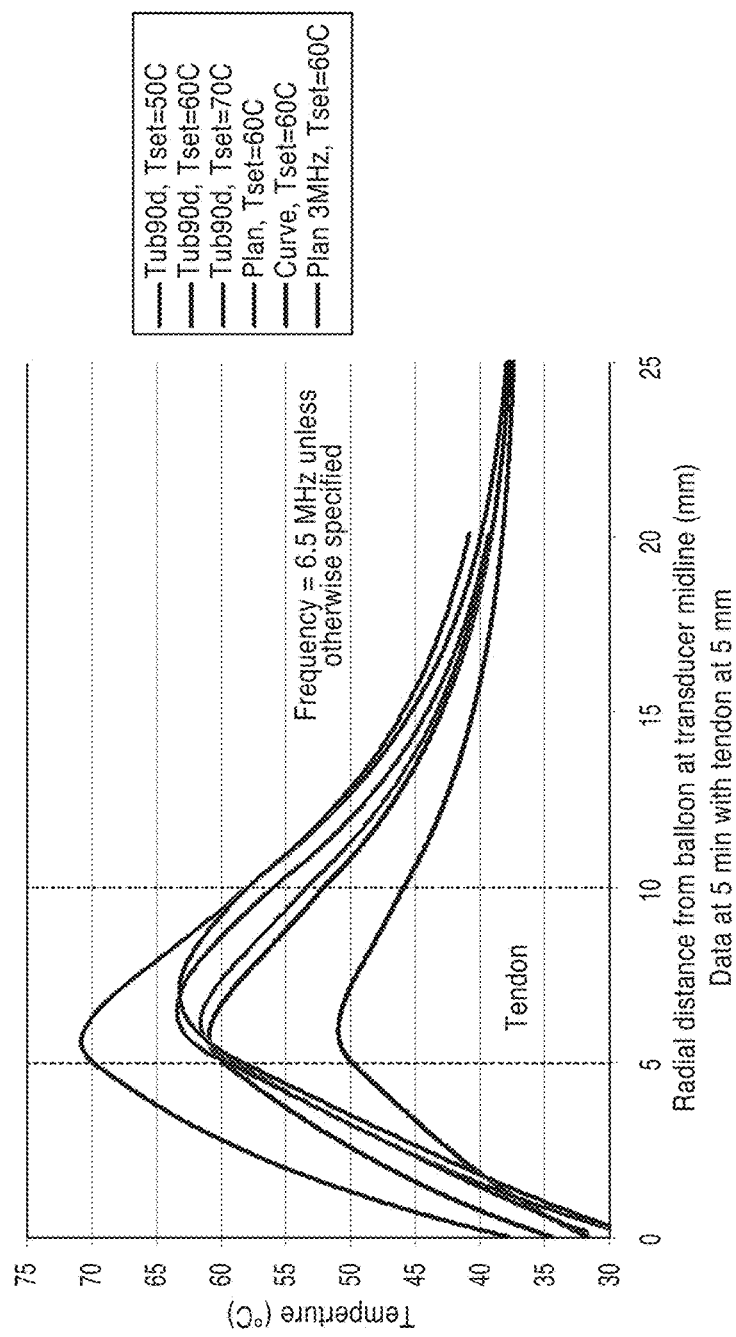

APPARATUS AND METHODS FOR TRANSURETHRAL TREATMENT OF STRESS URINARY INCONTINENCE

CROSS-REFERENCE TO RELATED APPLICATIONS

This application is a 35 U.S.C. § 111(a) continuation of PCT international application number PCT/US2013/048350 filed on Jun. 27, 2013, incorporated herein by reference in its entirety, which claims priority to, and the benefit of, U.S. provisional patent application Ser. No. 61/665,299 filed on Jun. 27, 2012, incorporated herein by reference in its entirety. Priority is claimed to each of the foregoing applications.

The above-referenced PCT international application was published as PCT International Publication No. WO 2014/004922 on Jan. 3, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to treatment of stress urinary incontinence (SUI), and more particularly to systems and methods for transurethral treatment of stress urinary incontinence.

2. Background Discussion

Treatment of Stress Urinary Incontinence (SUI) in females is an involuntary loss of urine that occurs during physical activity, such as coughing, sneezing, laughing, or exercise. The prevalence estimates range up to 72%, 6-11% for severe SUI. This accounts for >1 million office visits, $20 billion in direct and indirect costs in 2000.

The prominent cause of SUI is the weakening of the levator ani due to childbirth, nerve damage, or age which causes strain on endopelvic fascia and ligaments associated with the urethra. Strained connective tissue becomes more elastic, and results in urethral hypermobility: the posterior urethral wall descends in the pelvis rather than compress against the anterior wall during increased intra-abdominal pressure. Thus, transmitted intra-abdominal pressure can't close off the proximal urethra next to bladder neck.

Presently used technologies (laser, microwave, RF, etc.) have limitations due to fundamental physics and tissue interactions. Thermal ablation with these techniques may not be predictable or controllable (dynamic and heterogeneous tissue properties; direct interactivity with treatment energy source changes patterns). This presents difficulty in targeting the treatment site such that the target tissue is not properly treated, and surrounding healthy tissue is often damaged. Other limitations include limited treatment volume and potentially long treatment times.

BRIEF SUMMARY

An aspect of the technology described herein is application of ultrasound energy from a delivery catheter within the female urethra to target surrounding tissues for the treatment of stress urinary incontinence or other types of tissue remodeling from within the pelvic urethra.

Another aspect is a multi-sectored tubular, planar, or curvilinear ultrasound applicator configured for treatment of stress urinary incontinence or other types of tissue remodeling from within the pelvic urethra.

Another aspect is an ultrasound device configured to generate thermal therapy or acoustic means to affect targeted tissue remodeling or modification to target anatomy to treat stress urinary incontinence or other types of tissue remodeling from within the pelvic urethra. The acoustic means may comprise high acoustic energy with moderate heating—high intensity pulsed ultrasound.

Another aspect is the use of heat to induce tissue remodeling and increase the tissue density or stiffness of the endopelvic fascia or other tissue target to increase the resistance to urinary flow.

A further aspect is a lightly focused or directional ultrasound transducer or multi-sectored tubular (or array of transducers) transducer to heat the tissue to a prescribed temperature, at a prescribed depth, for a prescribed time.

Another aspect is treatment of the targeted section of anatomy via a transurethral applicator.

In one embodiment, the applicators of the technology described herein may be applied to the target anatomy via low temperature heating or high temperature heating, via acoustic energy without heating or with heating.

Another aspect of the technology described herein is to apply ultrasound energy to a treatment region most impacting for treating endopelvic fascia for SUI, e.g. at mid-50% of urethral length with insonation directed transurethrally laterally and posteriorly towards the vagina with penetration of 5-15 mm. Multiple sectors of tubular arrays can be used to treat simultaneously.

In another embodiment, a transurethral catheter provides targeted treatment zones outside urethra via an applicator with multiple sectors, urethral cooling balloon, and bladder positioning balloon for directed application in connective or muscle tissue of thermal lesions produced by simultaneous sonication or activation of two separate sectors from a tubular device. An inactive zone may be directed towards the vaginal wall or nerves.

Another embodiment comprises conformal ultrasound technology for high-intensity ultrasound treatment. Ultrasound treatment could comprise sonication of encapsulated drug or stiffening agent, as injected directly into tissue or IV. Acoustic energy alone and/or heat can be used to mediate the response.

Another embodiment is a bi-sectored tubular ultrasound catheter configured to achieve a thermal pattern that heats connective tissue while avoiding nerve bundles. The minimal separation between sectors that can achieve thermal protection of the nerves is desired.

Another embodiment is a bi-sectored tubular ultrasound catheter configured to achieve a thermal pattern that heats connective tissue while avoiding vaginal tissue. The minimal separation between sectors that can achieve thermal protection of the nerves is desired.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

Figure 13A:
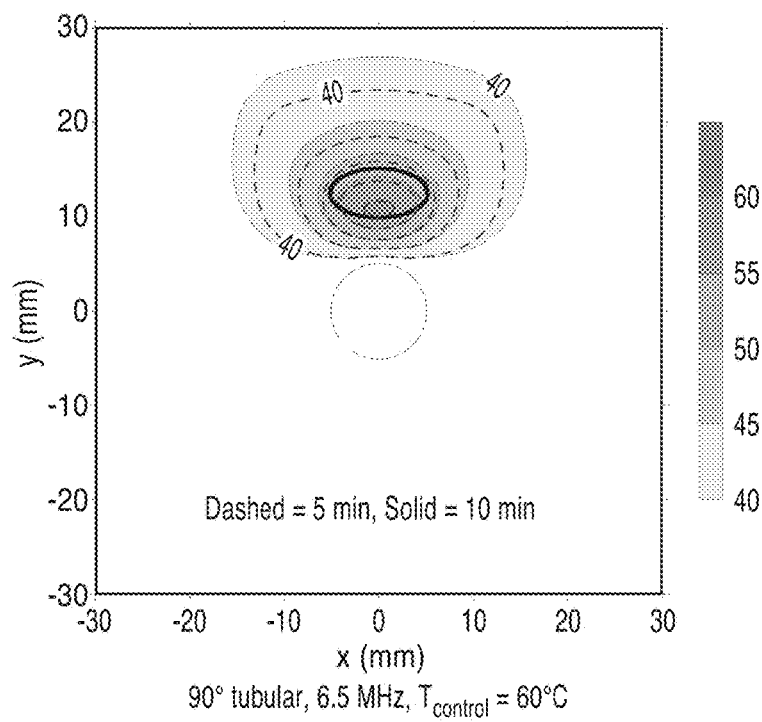
Figure 13B:
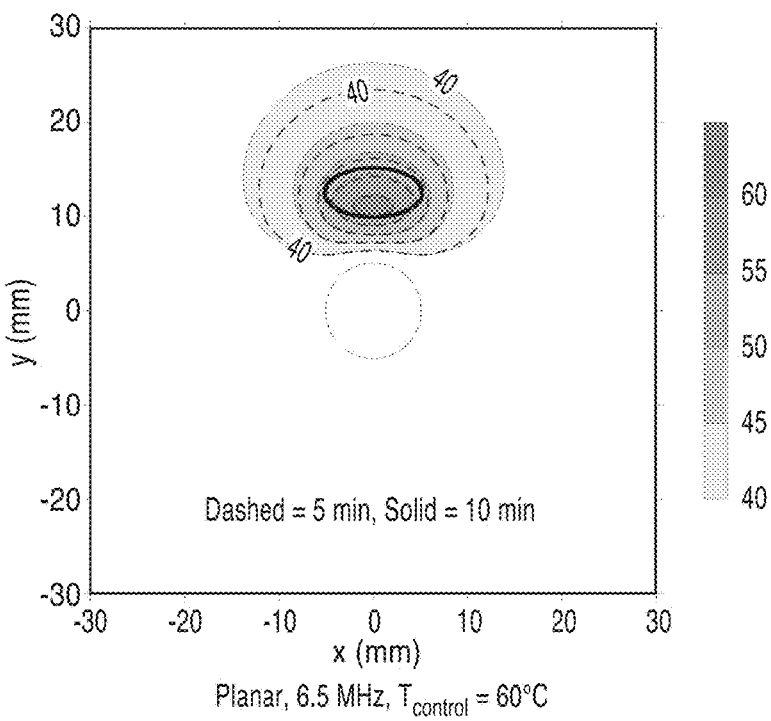
Figure 13C:
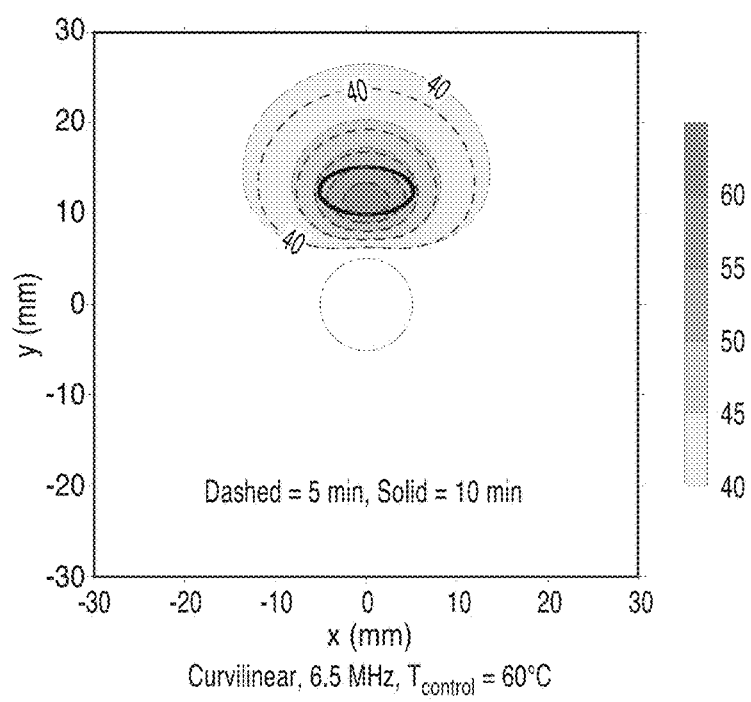

FIG. 13A, FIG. 13B, and FIG. 13C show a plot of the results for tubular, planar, and curvilinear transducers, respectively, at $T_{control}=60°$ C. and wall thickness of 5 mm.

Figure 14A:
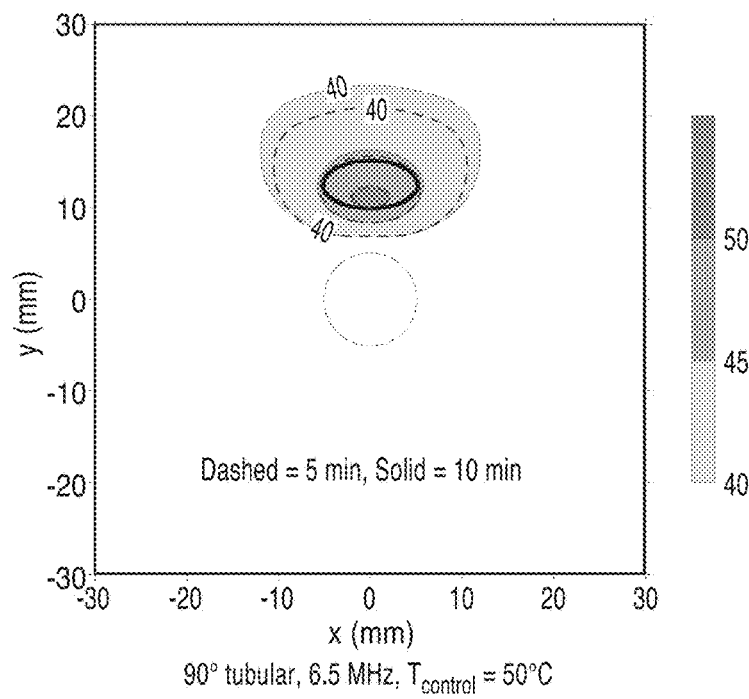
Figure 14B:
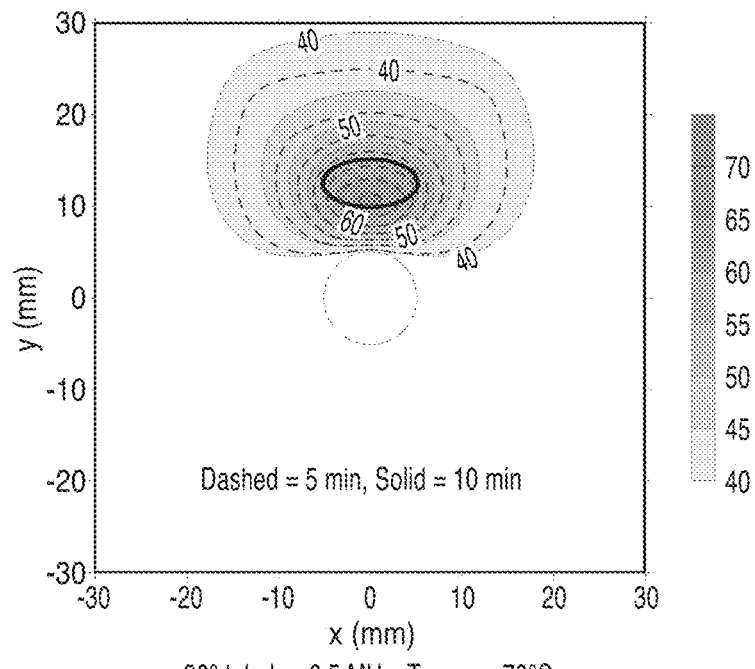
Figure 14C:
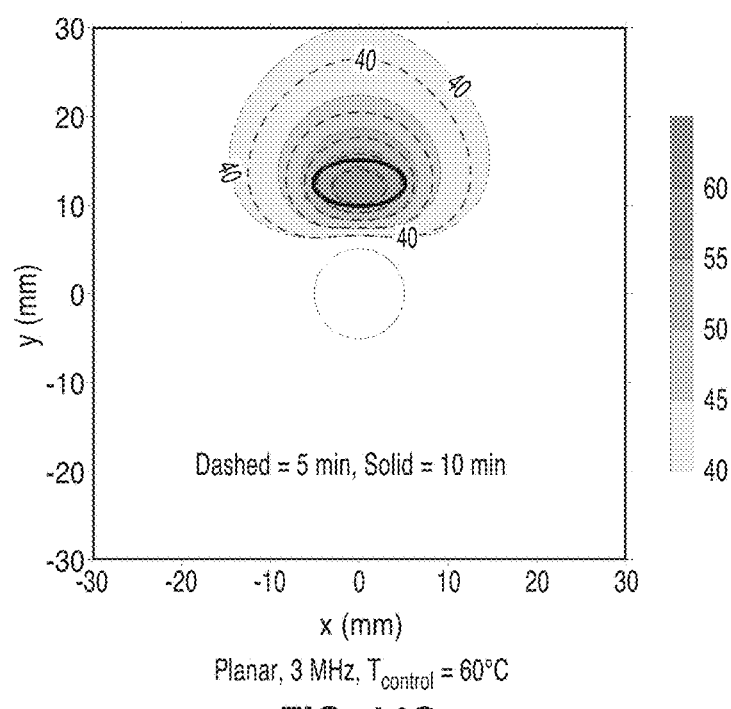

FIG. 14A, FIG. 14B, and FIG. 14C show a plot of the results for tubular, planar, and curvilinear transducers, respectively, for wall thickness of 5 mm at $T_{control}=50°$ C.-70° C.

Figure 15A:
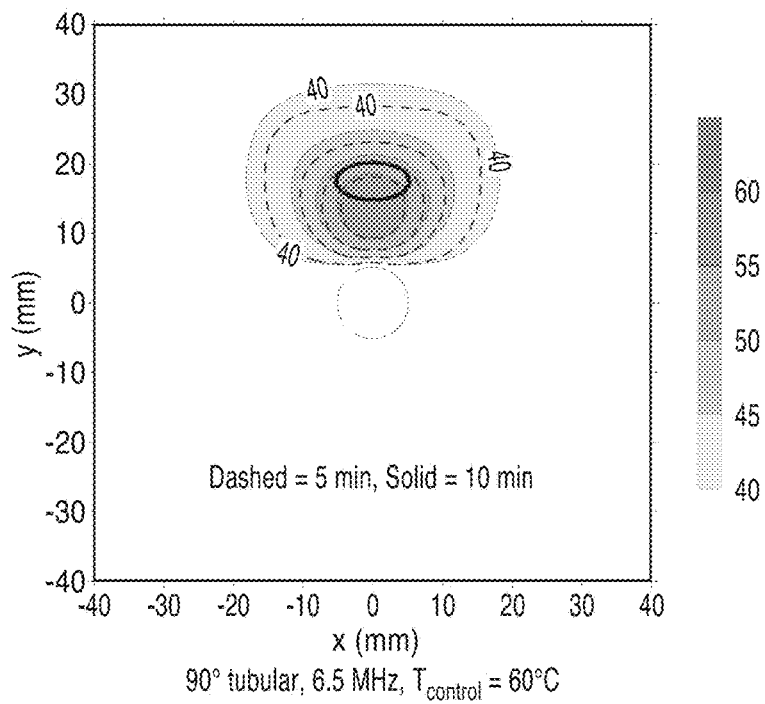
Figure 15B:
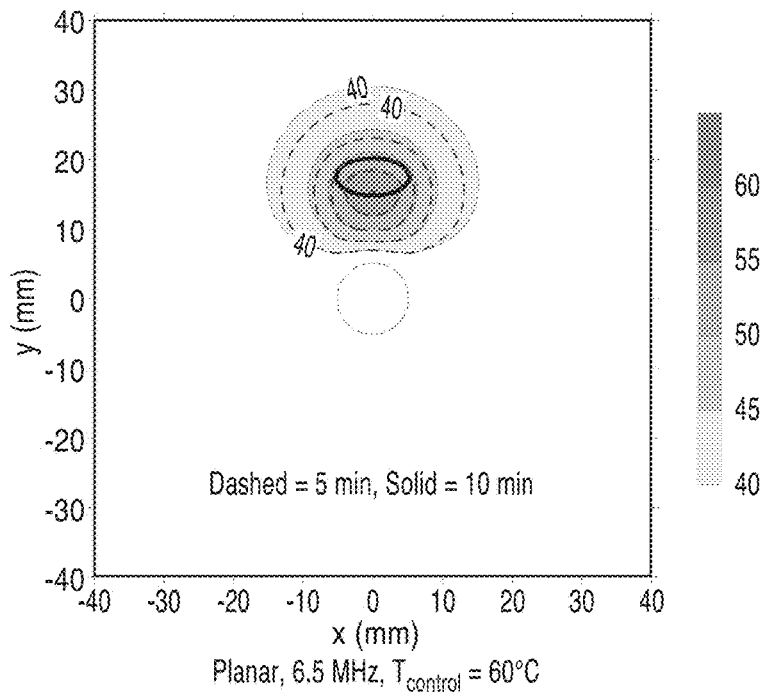
Figure 15C:
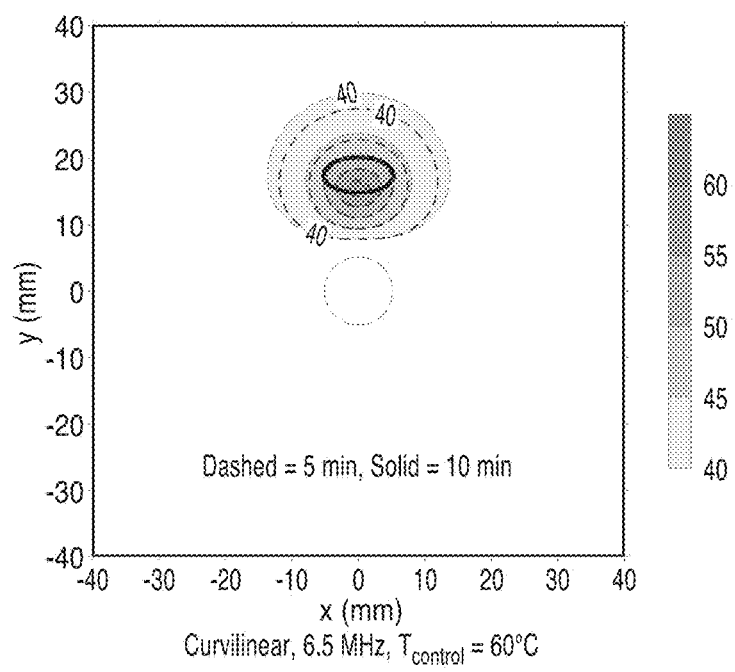

FIG. 15A, FIG. 15B, and FIG. 15C show a plot of the results for tubular, planar, and curvilinear transducers, respectively, at $T_{control}=60°$ C. and wall thickness of 10 mm.

FIG. 16A shows a plot of the radial distance from the balloon at 5 min with tendon at 5 mm.

Figure 16B:
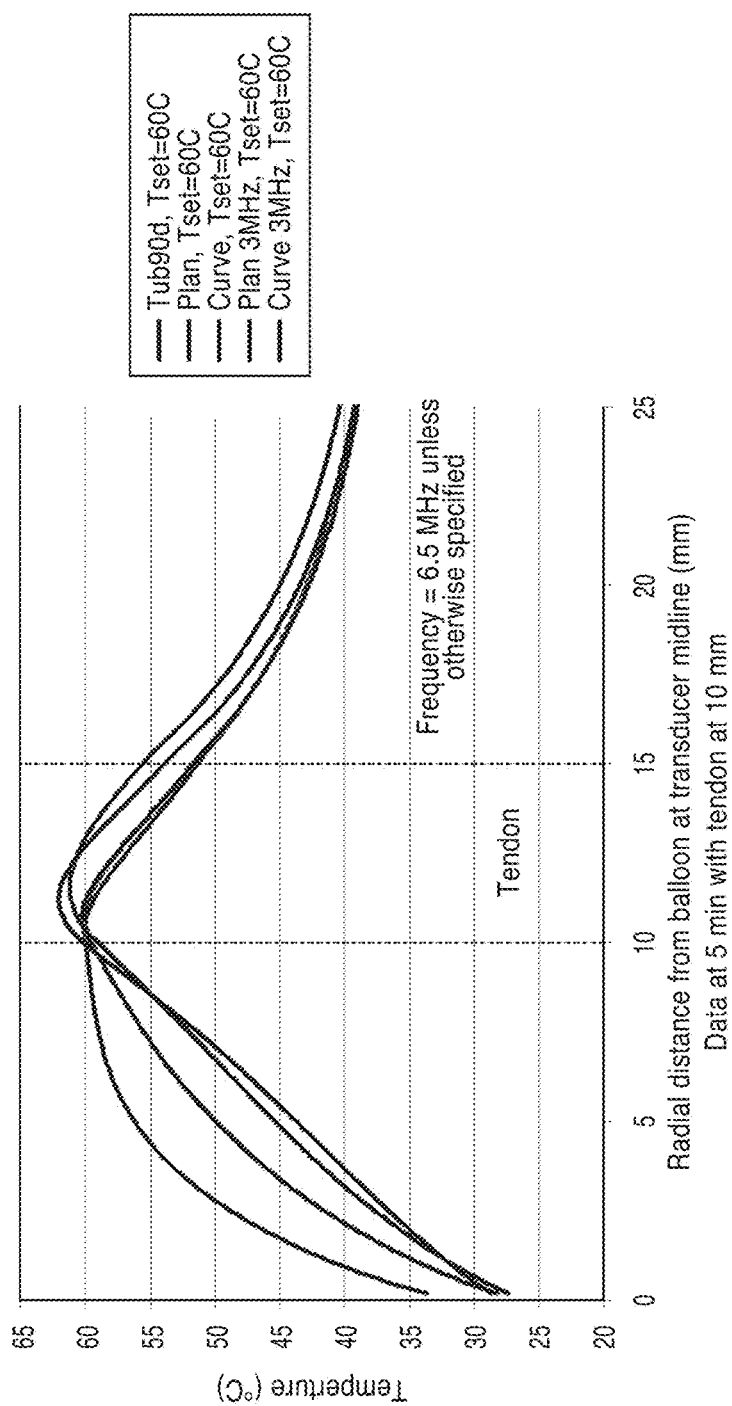
Figure 17A:
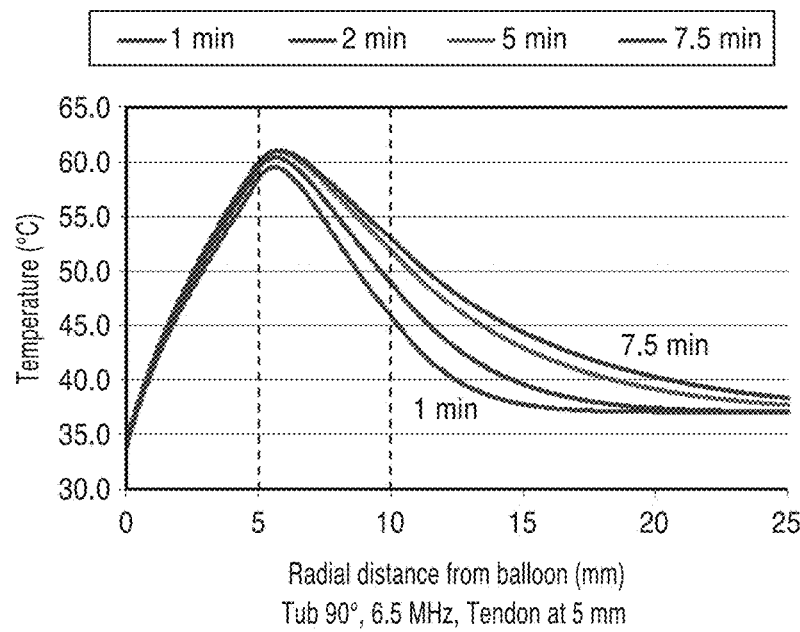
Figure 17B:
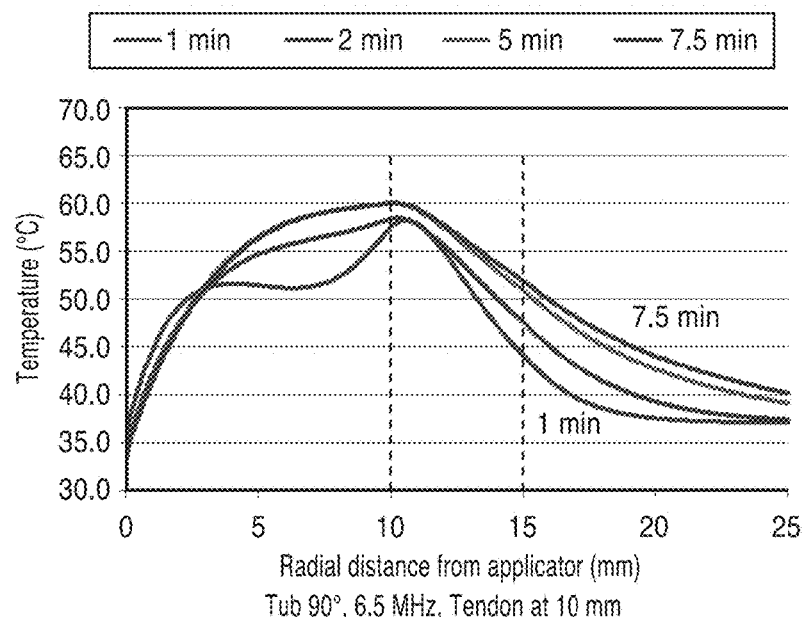
Figure 17C:
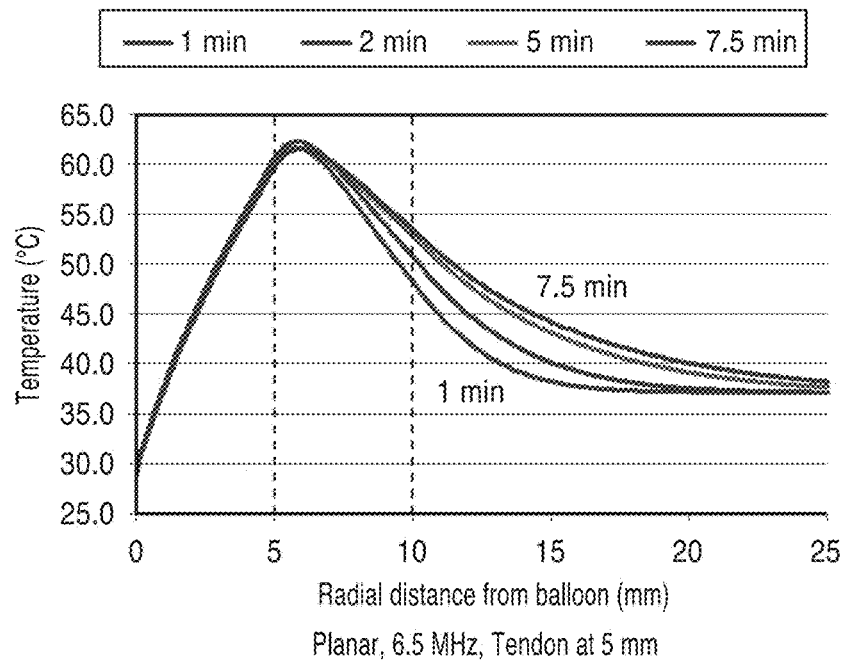
Figure 17D:
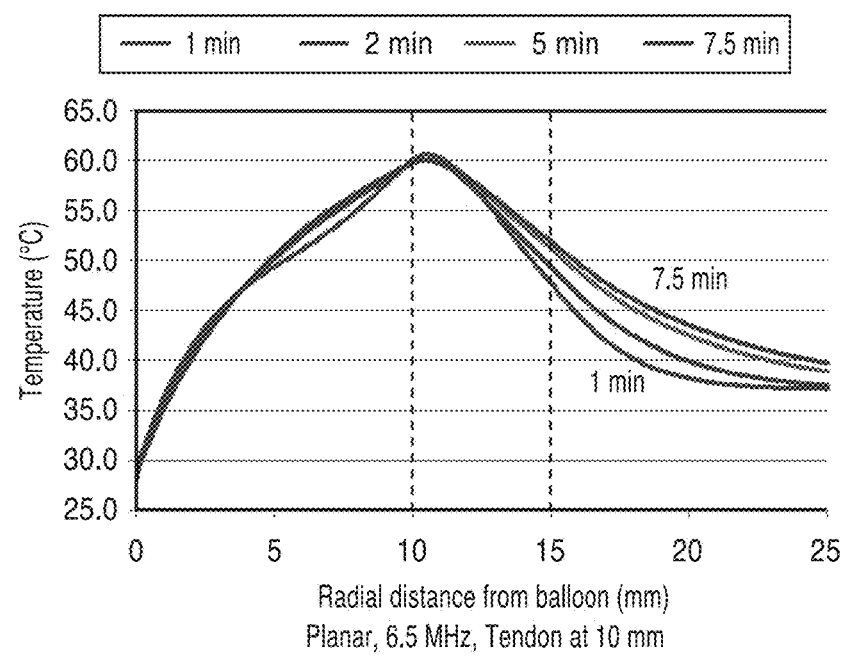
Figure 17E:
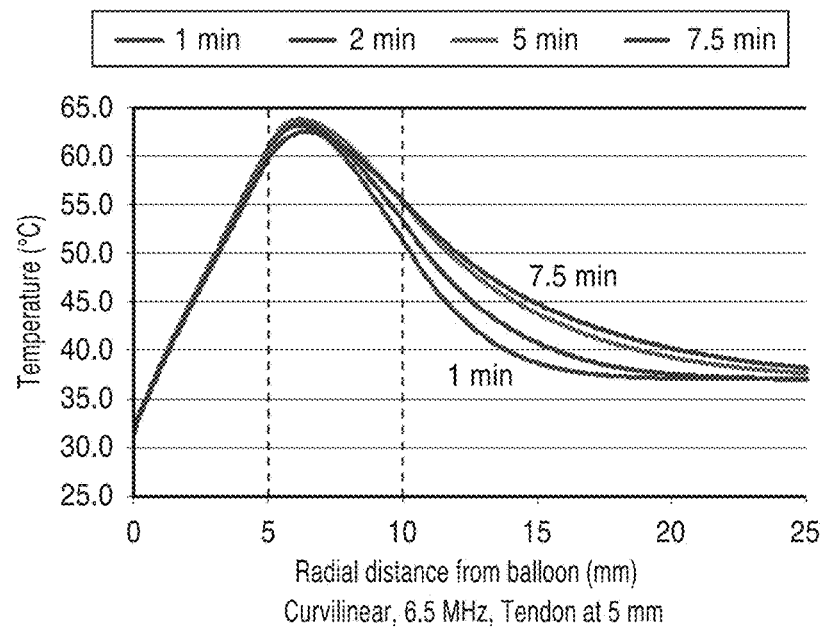
Figure 17F:
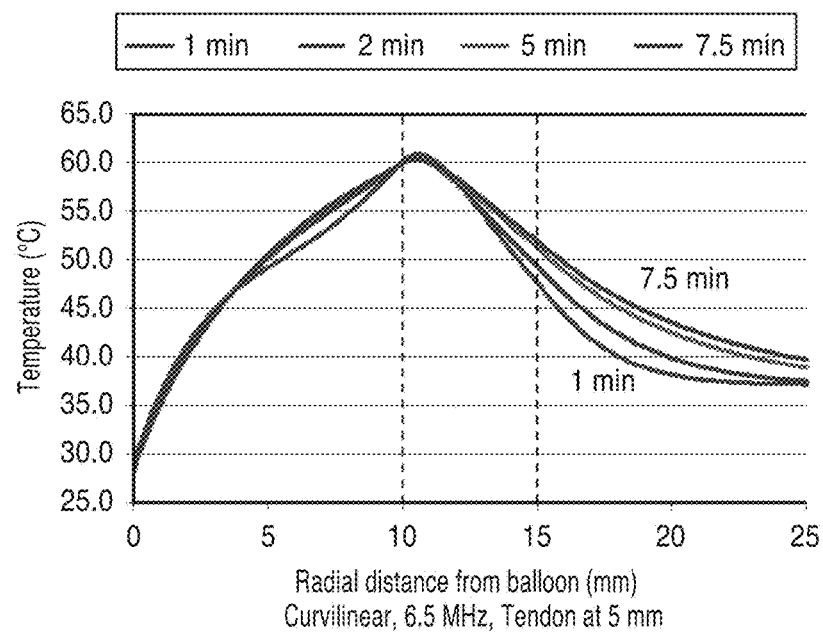

FIG. 16B shows a plot of the radial distance from the balloon at 5 min with tendon at 10 mm.

FIG. 17A through FIG. 17F show a comparison of heating for the tubular, planar, and curvilinear devices operating at 6.5 MHz with connective tissue at 5 mm or 10 mm from the balloon surface.

Figure 18A:
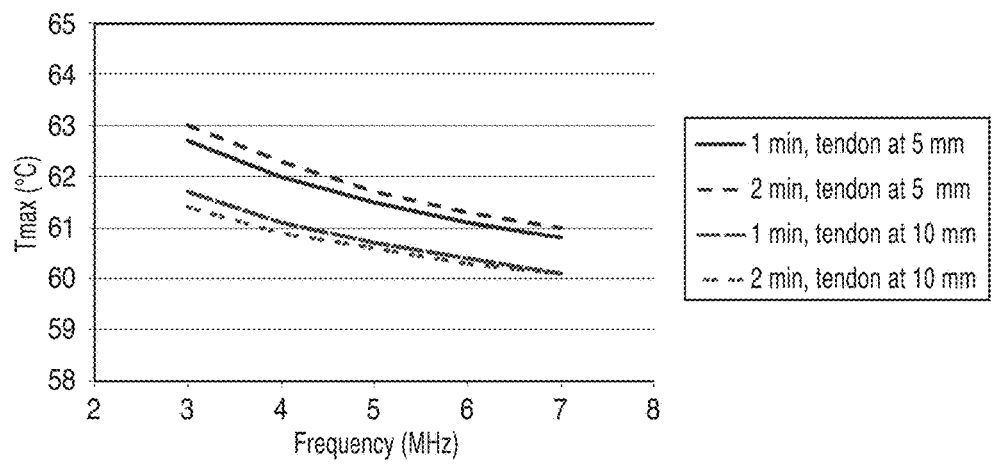
Figure 18B:
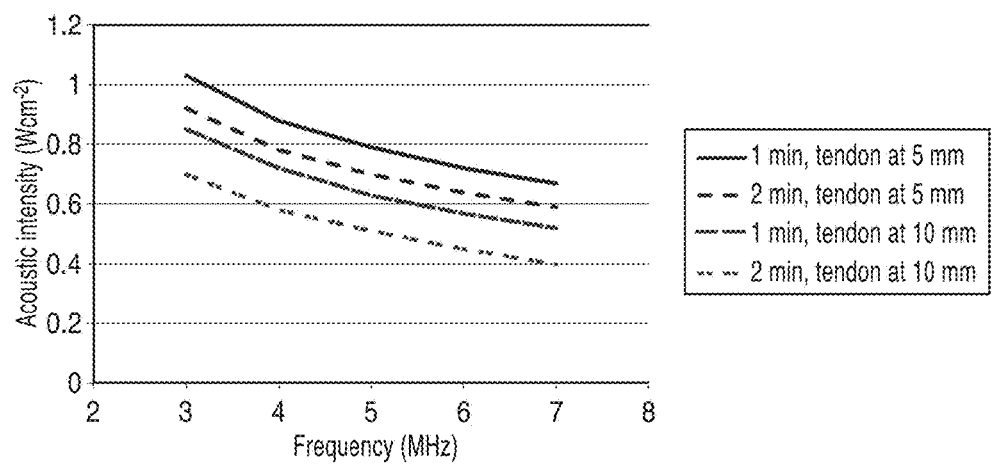

FIGS. 18A and 18B show plots of the maximum temperature and acoustic intensity with respect to frequency, respectively.

Figure 19A:
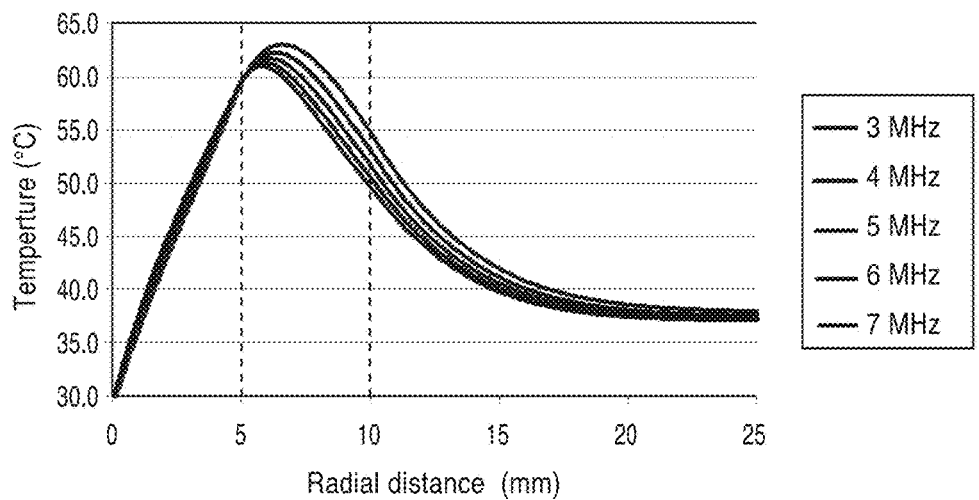
Figure 19B:
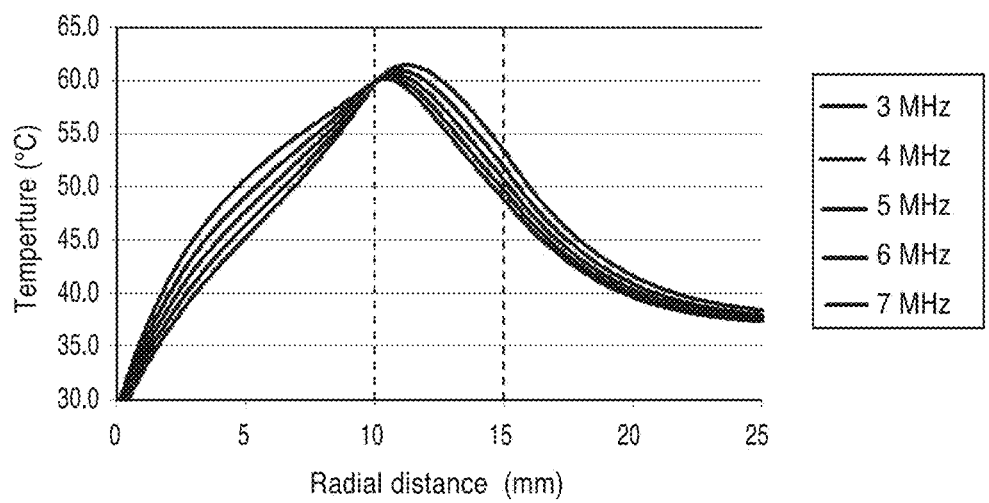

FIGS. 19A and 19B illustrate differences in urethral wall heating and heating of the connective tissue over the frequency range radial plots.

Figure 20A:
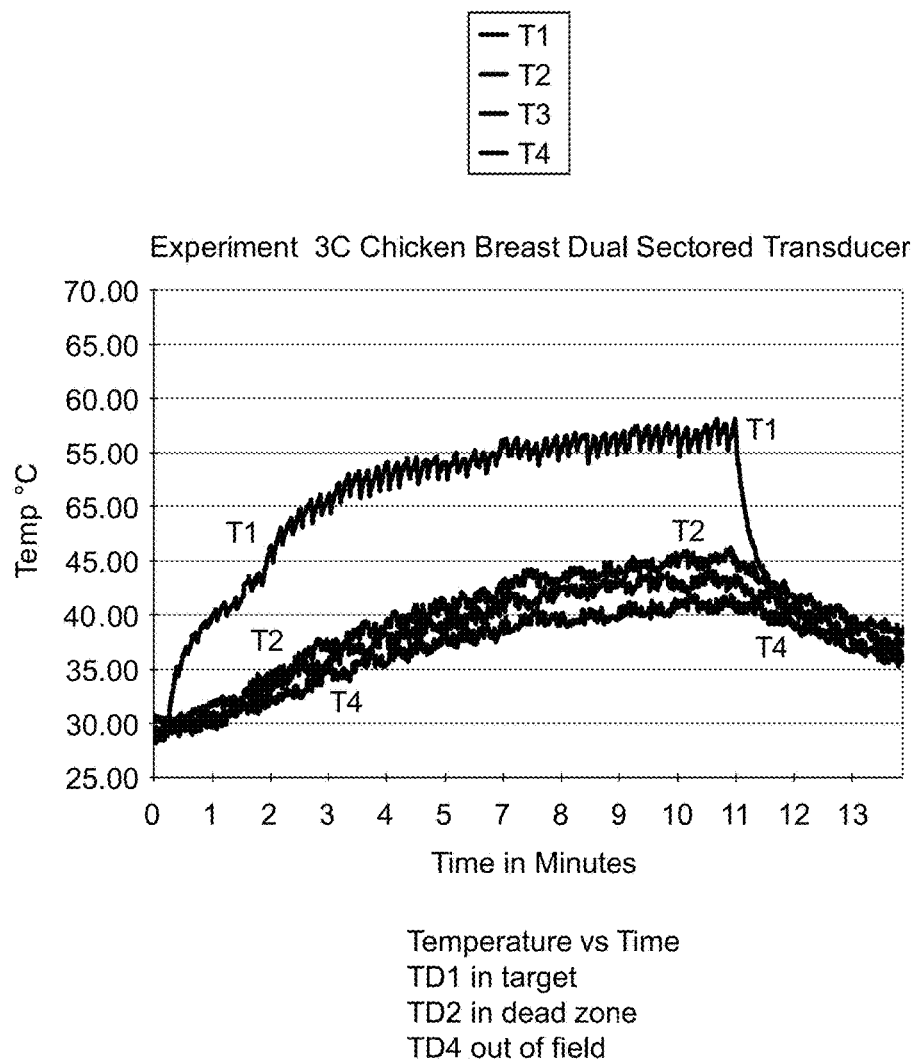
Figure 20B:
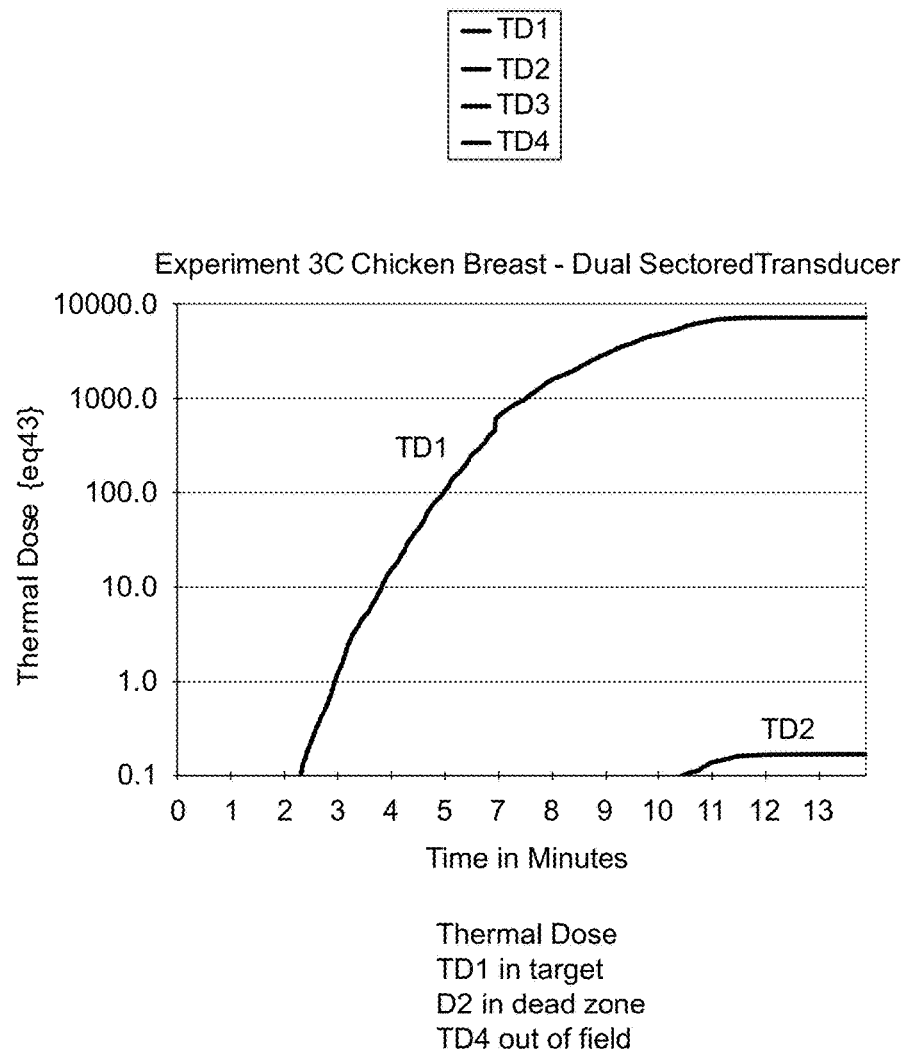

FIG. 20A and FIG. 20B show plots results for the ex vivo experiment for temperature vs. time (FIG. 20A) and thermal dose (FIG. 20B).

Figure 21A:
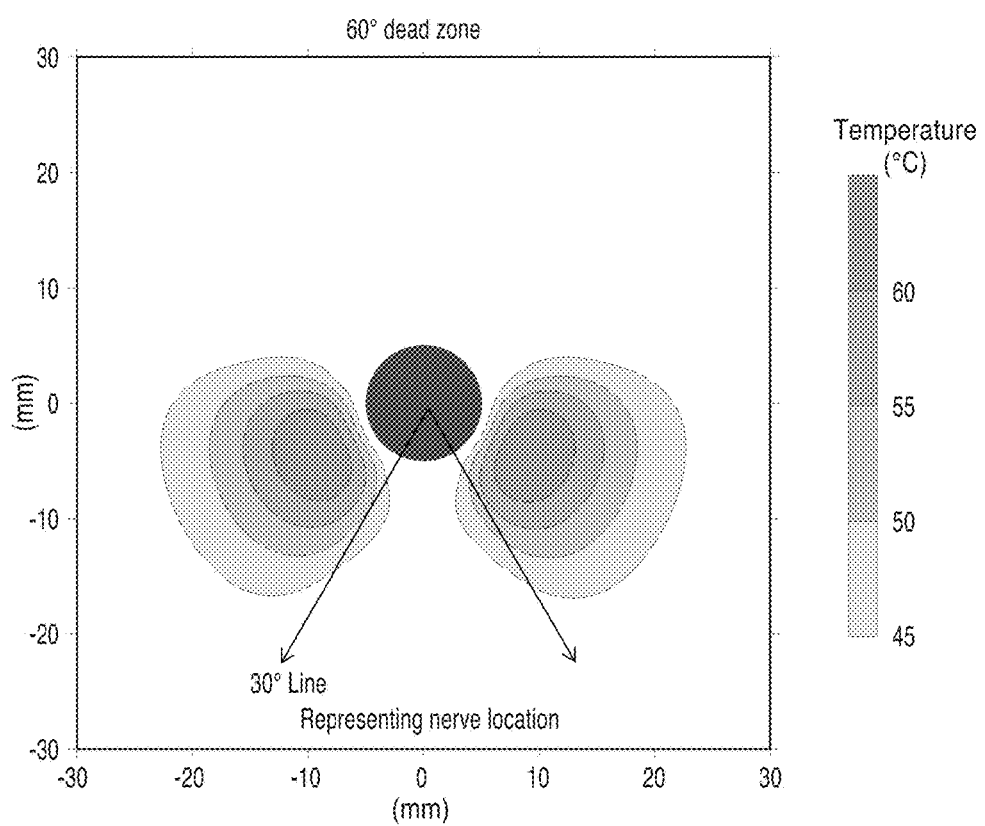

FIG. 21A shows the heating pattern isotherms for a dual-sectored transducer 12 having a 60° posterior dead zone.

Figure 21B:
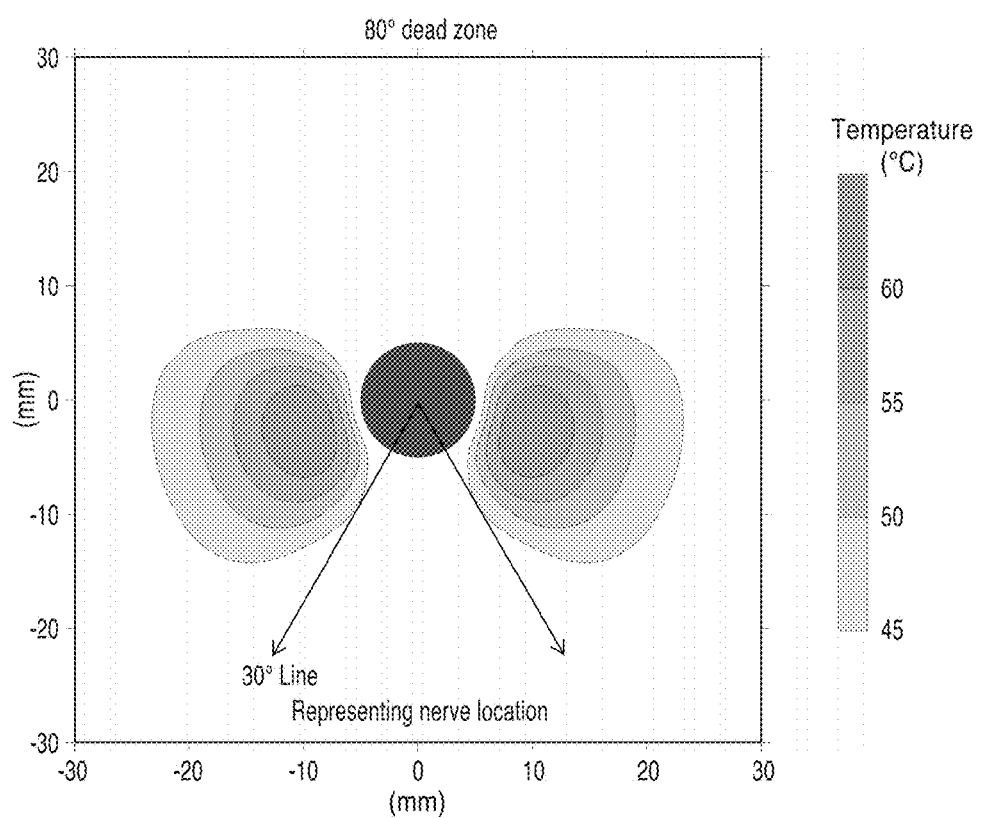

FIG. 21B shows the heating pattern isotherms for a dual-sectored transducer having an 80° posterior dead zone.

Figure 21C:
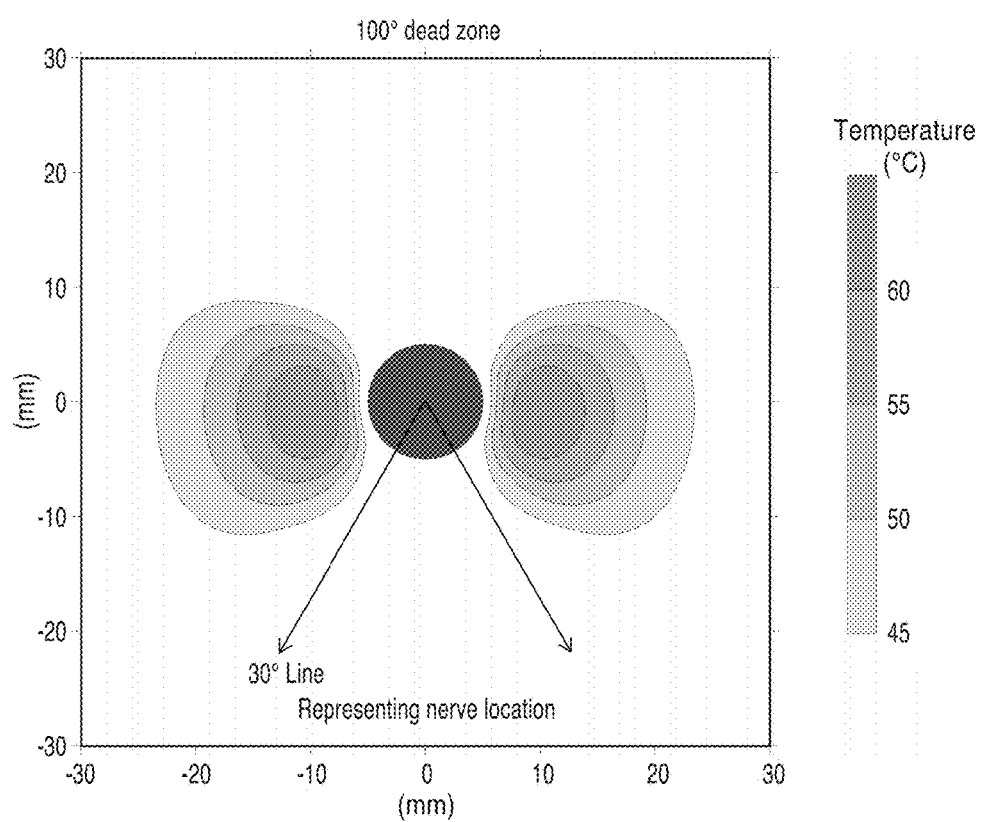

FIG. 21C shows the heating pattern isotherms for a dual-sectored transducer having a 100° posterior dead zone.

Figure 22A:
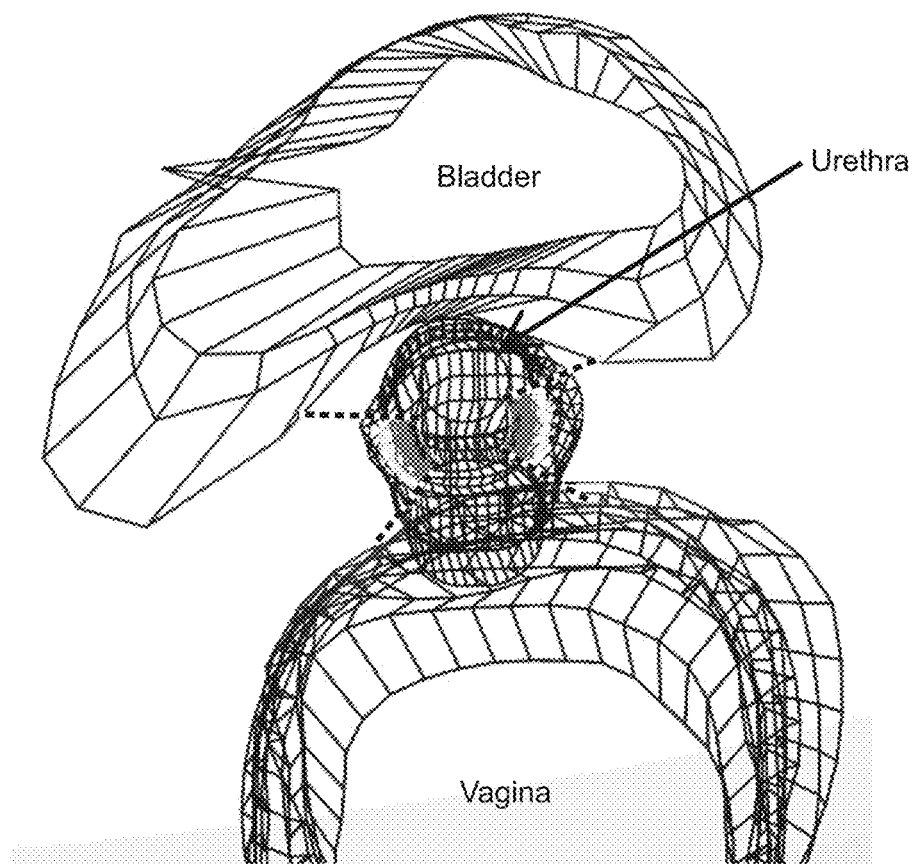

FIG. 22A shows an image for simulation of dual-sector, lateral 90 degree sonication.

Figure 22B:
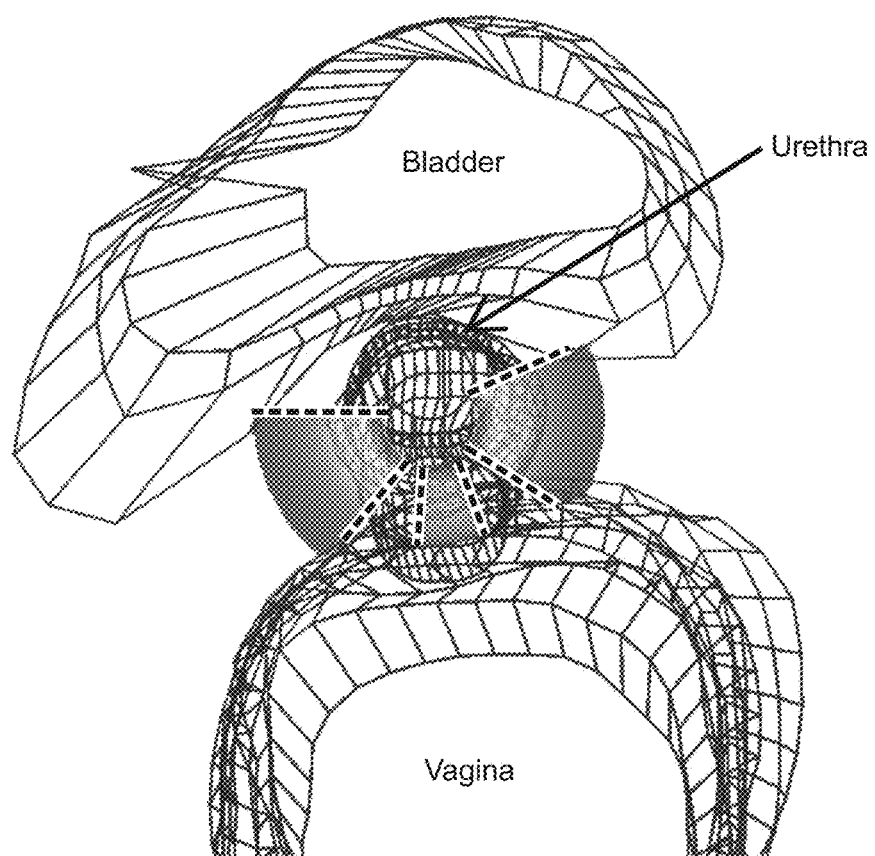

FIG. 22B shows an image for simulation of wide-angle triple-sector lateral 90 degree and posterior 60 degree sonication.

Figure 23A:
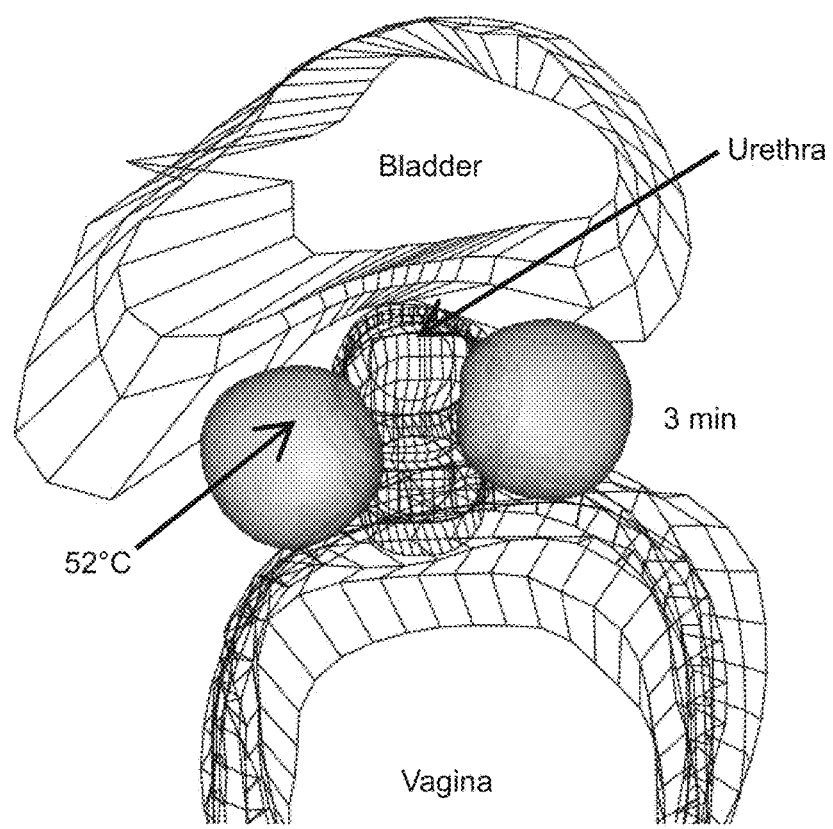

FIG. 23A shows an image for simulation of a 52° C. temperature/dose cloud at 3 min for simulation of a dual-sector dosing of FIG. 22A.

Figure 23B:
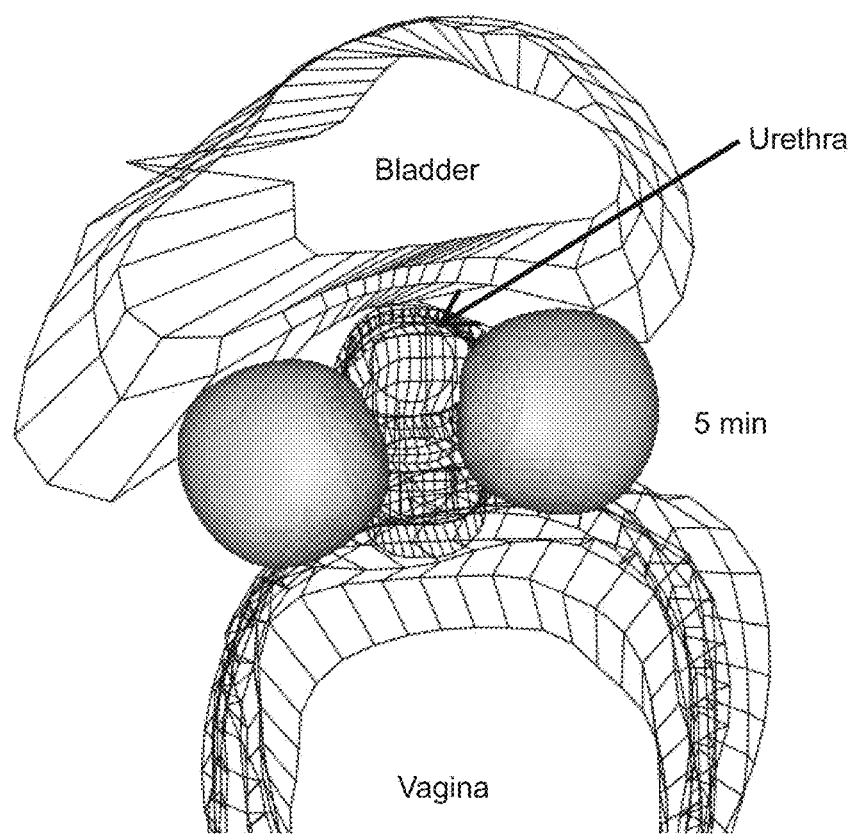

FIG. 23B shows an image for a simulation of a 52° C. temperature/dose cloud at 5 min for dual sector dosing of FIG. 22A.

Figure 24A:
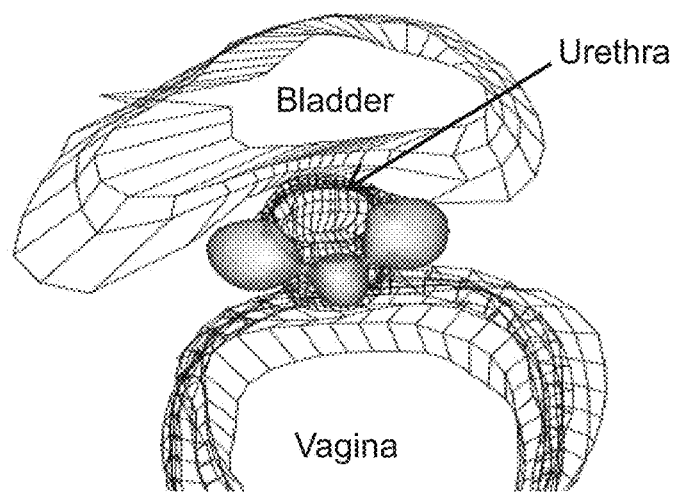

FIG. 24A shows an image for a simulation of a 52° C. temperature/dose cloud at 1 min for the wide-angle triple-sector dosing of FIG. 22B.

Figure 24B:
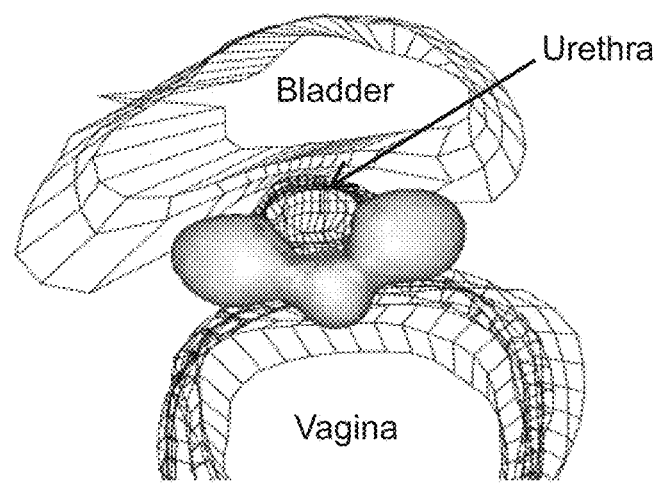

FIG. 24B shows an image for a simulation of a 52° C. temperature/dose cloud at 2 min for the wide-angle triple-sector dosing of FIG. 22B.

Figure 25:
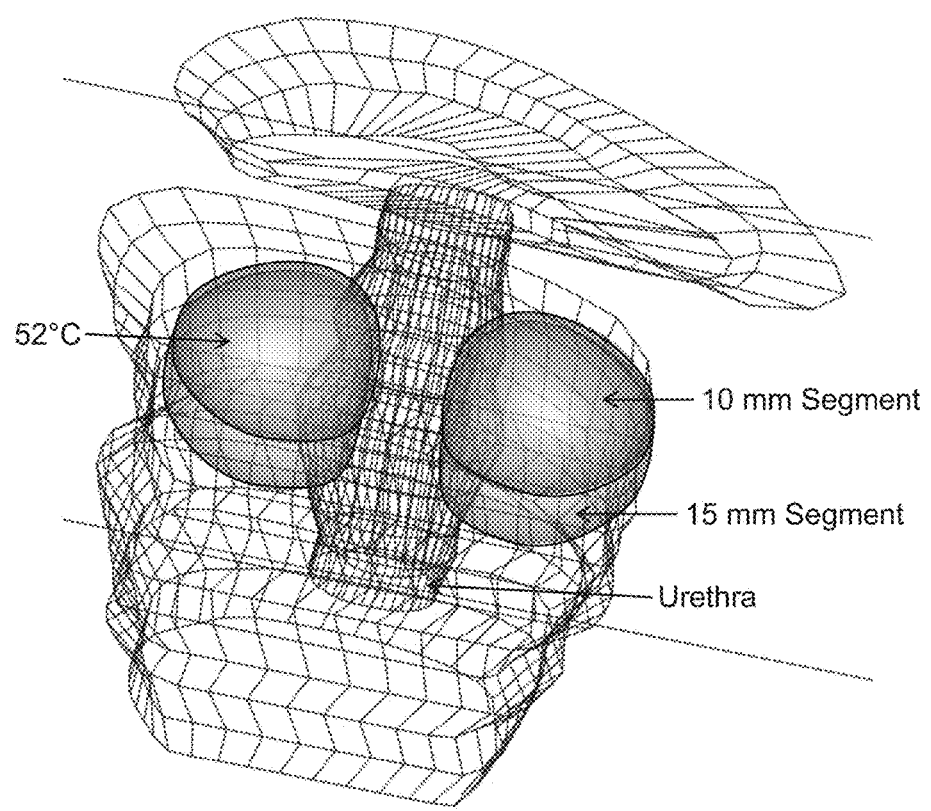

FIG. 25 shows an image for a simulation of 52° C. temperature/dose clouds for the dual-sector dosing of FIG. 22A at 14.5 W/cm2 for 10 mm and 15 mm transducers.

DETAILED DESCRIPTION

Figure 3:
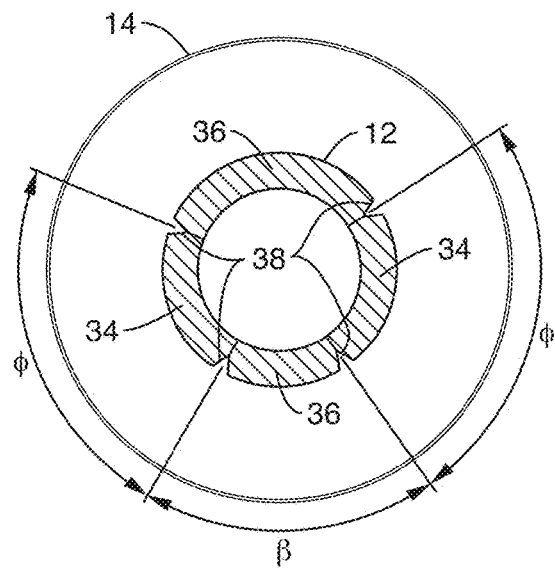
FIG. 3 illustrates a cross-sectional view of an exemplary transducer for the catheters of FIG. 1 and FIG. 4.
Figure 4:
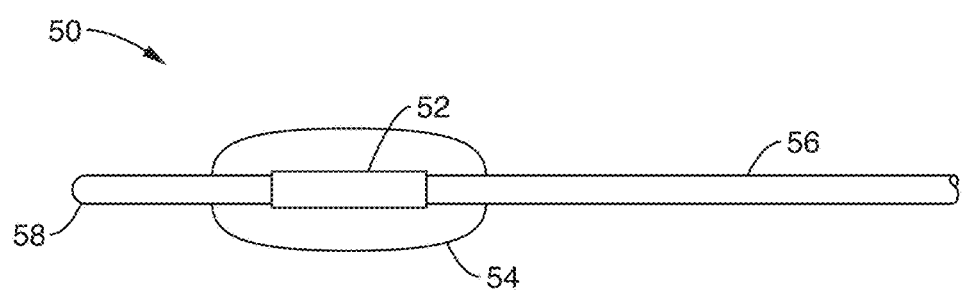
FIG. 4 illustrates an alternative embodiment of a catheter having a single transducer disposed within a cooling balloon on the distal end of a catheter body.
Figure 5:
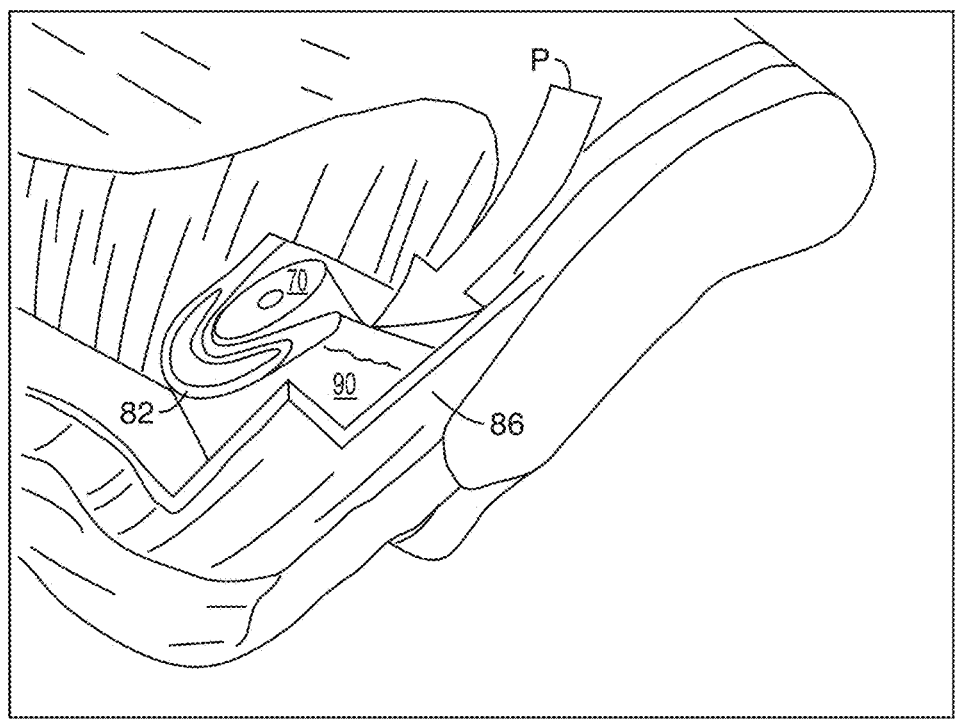
FIG. 5 is a perspective view of the bladder, vagina, and connective tissue.
Figure 9:
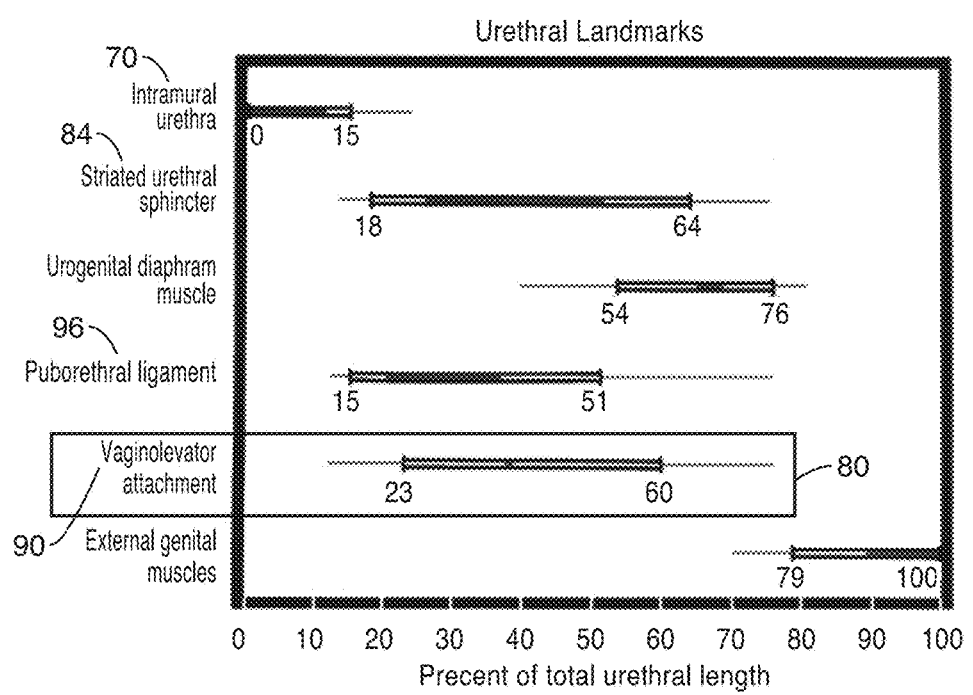
FIG. 9 is a graph showing anatomical landmarks of the pelvic anatomy along the length of the urethra.

FIG. 1 through FIG. 4 show embodiments of treatment devices configured for transurethral treatment of stress urinary incontinence by modeling/modification of specific anatomy illustrated in FIG. 5 though FIG. 9. The devices shown in FIG. 1 through FIG. 4 may be used interchangeably with the treatments methods shown in FIG. 10A through FIG. 11. FIG. 11 through FIG. 24 detail simulation and experimental data with respect to the use of devices of FIG. 1 through FIG. 4 and methods of FIG. 10A through FIG. 11 on tissue/simulated tissue corresponding to FIG. 5 though FIG. 9.

1. Transurethral Treatment Applicator Configuration

FIG. 1 through FIG. 4 show embodiments of treatment devices configured for transurethral treatment of stress urinary incontinence by modeling/modification of specific anatomy illustrated in FIG. 5 though FIG. 9.

Figure 1:
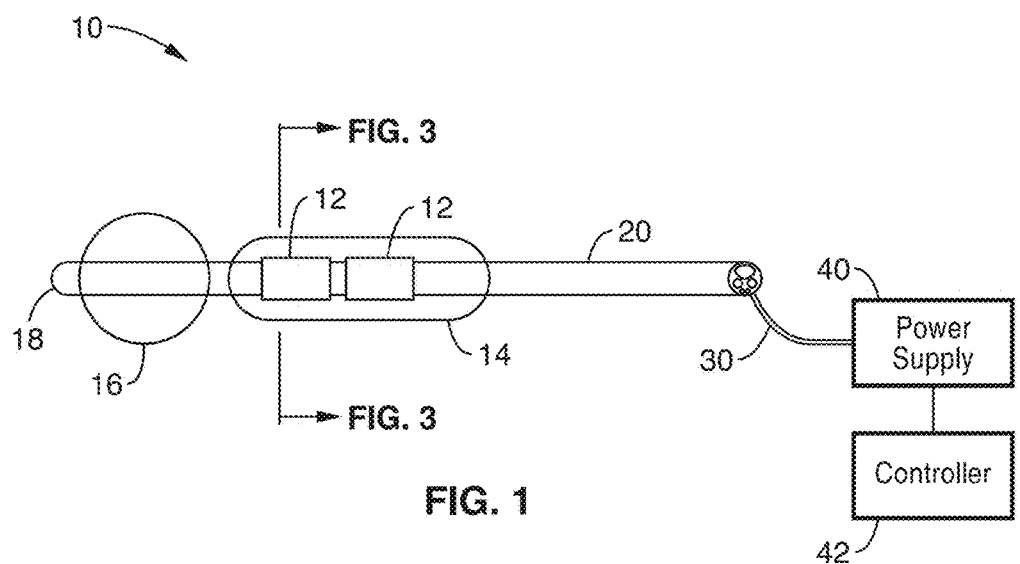
FIG. 1 shows a side view of a multi-lumen transurethral treatment catheter in accordance with the technology described herein.
Figure 2:
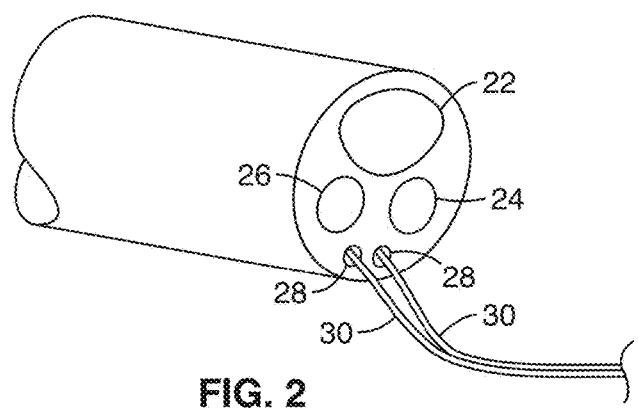
FIG. 2 is an expended view of the lumens of the catheter of FIG. 1.

FIG. 1 shows a side view of a multi-lumen transurethral treatment catheter 10 in accordance with the technology described herein. As seen in expanded detail view of FIG. 2, multi-lumen catheter 10 comprises an elongate body (e.g. flexible or rigid catheter) having separate channels for delivery of air, water and power to distal end 18 of the catheter, e.g., channel 24 for water inflow, channel 26 for water outflow, channel 22 for airflow to a coupling structure or balloon 14, and channels 28 housing wiring 30 to one or more transducers 12. In an alternative embodiment (not shown) the transducers are mounted on a larger polyimide tube surrounded by smaller polyimide splines to provide air-backing.

Catheter 10, and more specifically transducer leads 30, are preferably coupled to a power supply 40 and controller 42 for controlling various parameters of the ultrasound energy applied at transducers 12.

It is generally appreciated that balloon 14 be expanded within the urethra to provide cooling liquid flow to the immediate urethral tissue. Balloon 16, at distal end 18 of catheter body 20, may be inflated to provide anchoring of the catheter 10.

In an exemplary embodiment, the ultrasound transducers 12 are preferably sealed at the edges with heat-cured silicone (not shown) and covered with a layer of soft epoxy and PET heat-shrink tubing (not shown). While catheter 10 is shown in FIG. 1 as having a two-transducer array, it is appreciated that any number (e.g. 1 or greater), may be individually wired to power supply 40 and controller 42 for independent control of transducers 12 and precise axial control of energy delivery to the target anatomy.

FIG. 3 illustrates a cross-sectional view of an exemplary sectored tubular transducer 12 for devices 10 of FIGS. 1 and 50 of FIG. 4. As shown in FIG. 3, transducer 12 has been notched with longitudinal grooves 38 to give two active sectors 34 (e.g. emanating radially outward at $\phi=90°$) separated by an inactive zone 36 (e.g. emanating radially outward at $\beta=60°$, generally pointing downward or posteriorly toward the vaginal wall, as will be described in further detail below) configured to limit heating of the vagina and nerve bundles when the catheter 10/50 is positioned in the urethra (along with opposing 120° inactive zone 36 in the anterior direction). An exemplary emission pattern for such a bi-sectored transducer 12 may be seen with reference to FIG. 22A.

The anterior opposing inactive zone 36 is not necessarily directed to protecting sensitive tissue, but may be implemented so as to not needlessly treat tissue having little or no impact on the condition to be treated. It is contemplated the anterior inactive zone 36 not be used, resulting in one contiguous active zone of a 270°-300° swath that straddles the posterior inactive zone 36.

It is appreciated that the angle $\phi$ the active zones 34 and angle $\beta$ of the inactive zones 36 may be varied according to patient anatomy. Furthermore, for multi-transducer devices (e.g. catheter 10 of FIG. 1), transducers may be variably configured (e.g. one transducer having $\phi=100°$ and a second transducer having $\phi=80°$) to vary emission according to varying anatomy along the length of the treatment zone along the length of the urethra.

Furthermore, it is appreciated that any number of treatments sectors may be used. For example, a tri-sectored configuration, such as that shown in the emission pattern of FIG. 22B may also be used. In multi-sectored configurations, as detailed above, it is appreciated that the active sectors emit ultrasound therapy, simultaneously, so as to limit treatment time.

It is to be appreciated herein that each transducer sector 34 may be individually wired and in effect an independently actuatable transducer, though shown and described as subparts of an overall transducer 12 for illustrative simplicity. Corresponding transducer regions 34 may be all actuated simultaneously along the array, without actuating the inactive regions 36. Transducers 12 may also comprise phased arrays—i.e. multiple small transducer segments with separate phase control to steer and focus or generate a beam pattern.

Alternatively, it is contemplated that a single-sector 34 configuration (e.g., one treatment zone at $\phi=90°$, (not shown)) may be employed where one treatment zone is applied first (e.g. at a location a specified distance and orientation from a midline median or sagittal plane), and the catheter body 20 is then rotated axially (e.g. across inactive zone 36 ($\beta=60°$) at an opposing location a specified distance from midline median or sagittal plane) to treat an opposing treatment zone. The transducer 12 may be turned off during rotation, or left on while the applicator 10/50 is swiftly rotated through the anterior or posterior inactive zones (with minimal heating to protected tissues. It is appreciated that this configuration would double the overall treatment time, and thus may not be ideal.

It is also appreciated that the sectoring of the transducer may be achieved via a number of methods available in the art (e.g. other than notching, inactive sections 36 may comprise sections having an outer circumferential layer removed, or a covering, to affect a dead zone).

Furthermore, although the sectored tubular transducer of FIG. 3 is preferred embodiment, other configurations/geometries are contemplated. Examples include planar or plate, or curvilinear (e.g. hemispherical, or portions of cylinders (convex), or concave sections) depending upon the desired energy delivery. Many of the experiments detailed below with respect to FIGS. 12-25 are conducted with planar and curvilinear applicators, in additional to tubular applicators.

In one embodiment (not shown), two curvilinear applicators having a convex outer surface may be placed in axially parallel orientation and angularly adjacent to each other within a catheter body on either common or separate backings. The convex surfaces may be radial segments that generate divergent energy patterns, are rotated outward with respect to each other to generate a pair of separated active treatment zones (e.g.) $\phi=90°$, straddling an inactive zone 36 (e.g. $\beta=60°$). Parallel planar segments may be similarly configured to achieve spaced apart active treatment zones. Concave curvilinear segments may also be used to create spaced-apart converging energy patterns.

FIG. 4 illustrates an alternative embodiment of a catheter 50 having a single transducer 52 disposed within cooling balloon 54 on distal end 58 of catheter body 56. Catheter 50 may comprise a single-lumen catheter with polyimide tubing 56 to conduct water inflow and outflow to the cooling balloon 54.

In one embodiment, an exemplary catheter 10 comprises 3.5 mm (outside diameter (OD)) transducer 12, 10 mm OD balloon 14, and 4 mm catheter body 20, and catheter 50 comprises 2.5 mm (outside diameter (OD)) transducer 52, 10 mm OD balloon, and 2.8 mm catheter body 20 (see Table 1, showing dimensions for an exemplary embodiment of catheter 10 as "TRUS2" and an exemplary embodiment of catheter 50 as "TRUS1"). It is appreciated that the dimensions detailed in Table 1 are for reference purposes only, and may vary accordingly.

2. Target and Non-Target Anatomy

Figure 10A:
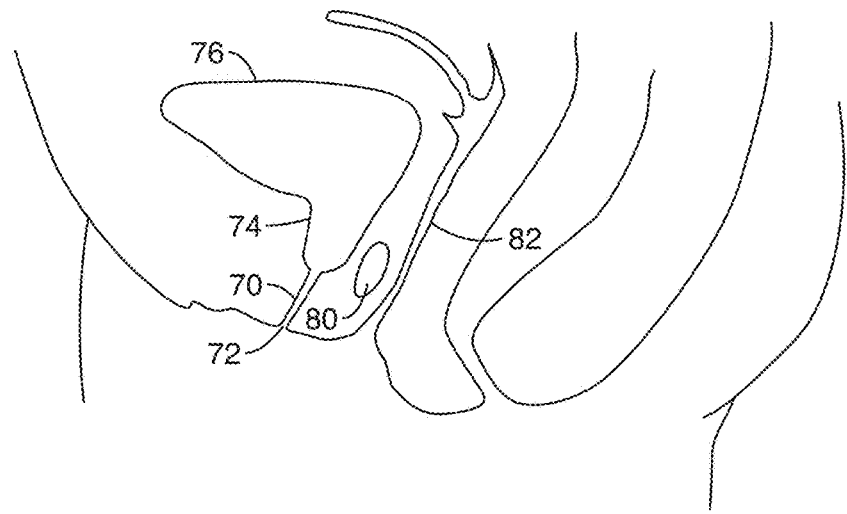
FIG. 10A shows a sagittal section view of the bladder, urethra, and surrounding anatomy of a female patient.
Figure 10B:
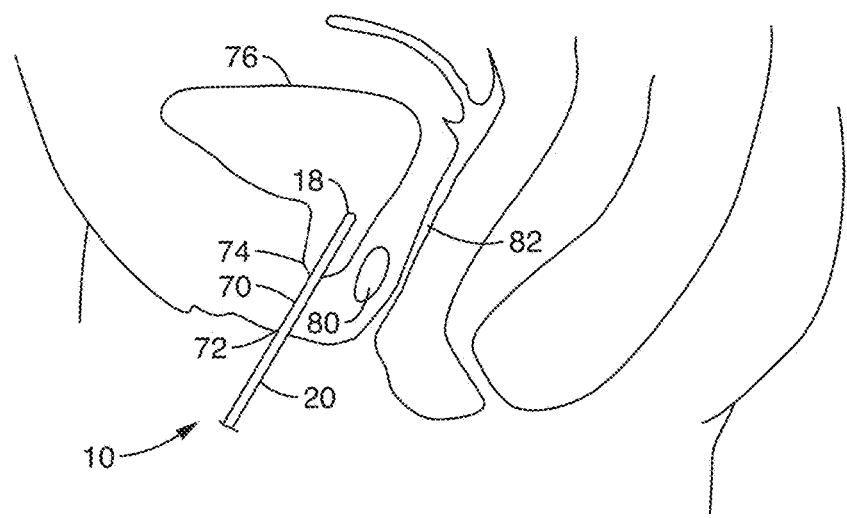
FIG. 10B is a schematic diagram of the catheter of FIG. 1 inserted transurethrally into the bladder of a patient.
Figure 10C:
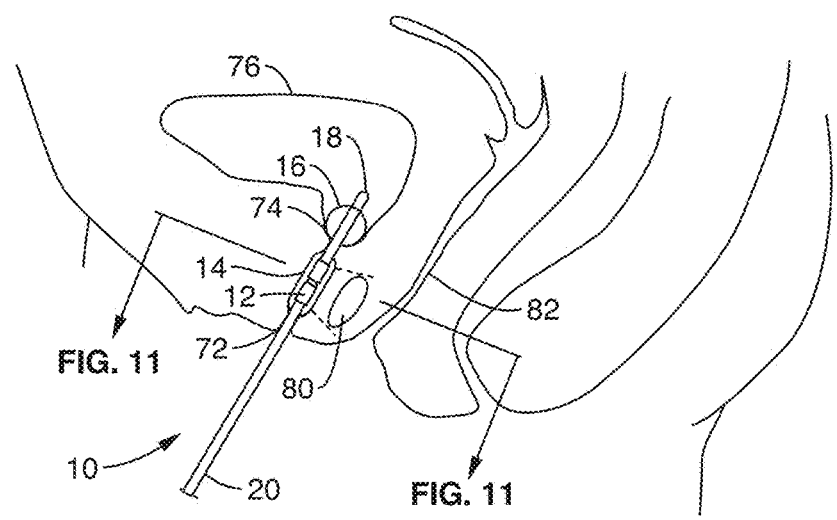
FIG. 10C is a schematic diagram of a preferred embodiment of the catheter of FIG. 1 being deployed in the bladder and urethra.
Figure 10D:
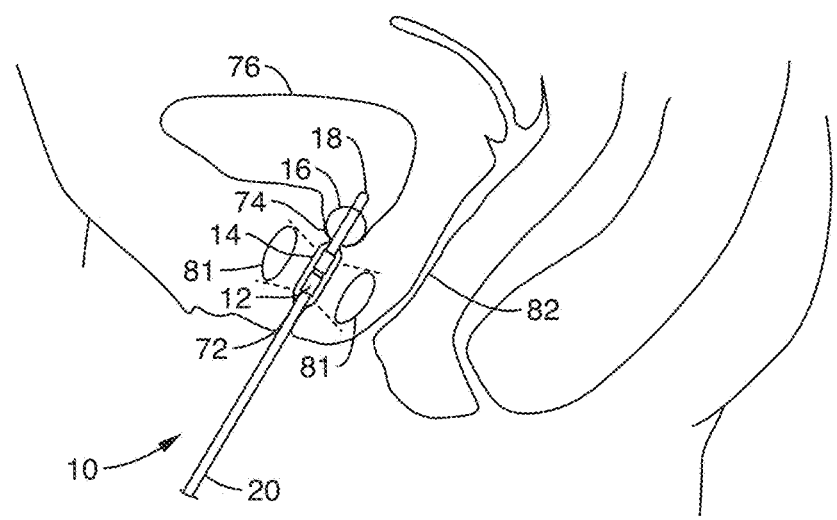
FIG. 10D is a schematic diagram of an alternative embodiment of the catheter of FIG. 1 being deployed at the proximal urethra.
Figure 11:
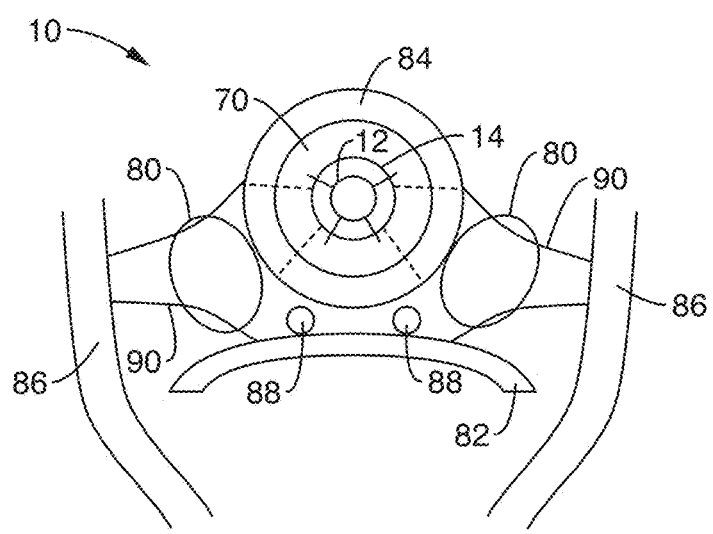
FIG. 11 is a cross-sectional view of the embodiment shown in FIG. 100.

FIG. 5 though FIG. 9 illustrate target anatomical features for therapeutic treatment using the devices of FIG. 1 through FIG. 4 and methods of FIG. 10A through FIG. 11, along with non-target features to be shielded/protected from treatment.

Referring to FIG. 5 through FIG. 9, increased intra-abdominal pressure P, such as from sneezing or coughing, forces the urethra against the vaginal wall and endopelvic fascia 90, relying on its stiffness to support the urethra. A premise of the method of the technology described herein (i.e. the Hammock Hypothesis) is that the levator ani 86 ("hammock") pulls the rectum, vagina 82, and urethra 70 towards pubic bone 98 (see FIG. 6) to aid urethral closure and prevent undue strain on connective tissue.

Figure 6:
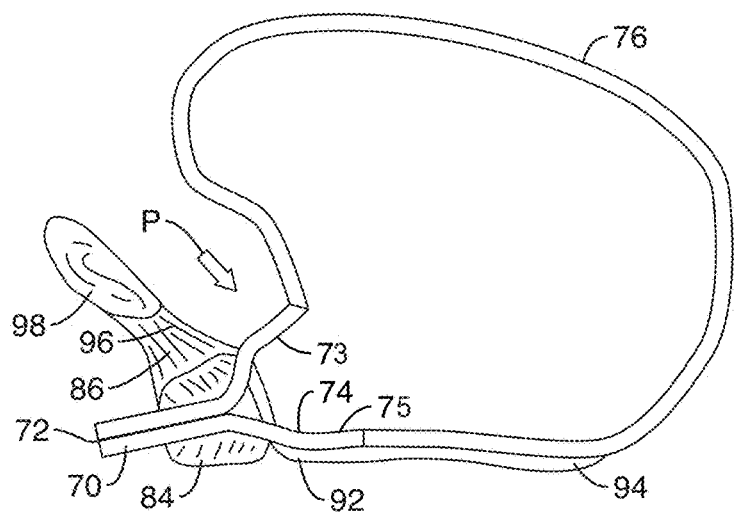
FIG. 6 is a sagittal cross-section view of the bladder, urethra, and surrounding anatomy.

Referring to FIG. 6, which shows a cross section (e.g. in the sagittal plane) of the bladder 76 and urethra 70, the urethra 70 is supported posteriorly at wall 75 at the proximal urethra 74 by the anterior vaginal wall 82, which is connected to tendinous structures and musculature by endopelvic fascia 90 (vaginolevator attachment). Weakening of the levator ani 86 due to childbirth, nerve damage, or age may cause strain on endopelvic fascia 90 and ligaments associated with the urethra 70. This strained connective tissue 90 becomes more elastic, and results in urethral hypermobility, i.e. the posterior urethral wall 75 of urethra 70 descends in the pelvis, rather than compress against the anterior wall 73 during increased intra-abdominal pressure. Connective tissues (endopelvic fascia) illustrated in FIG. 6 include pub-ourethral ligament 96 at one side of levator ani 86, urethropelvic ligament 92 the externally adjacent to posterior urethral wall 75, and the pubocervical ligament 94 externally adjacent to the bladder 76. The urethral wall 70 generally consists of layers of mucosa, smooth muscle (circular and longitudinal), and striated muscle.

Figure 7:
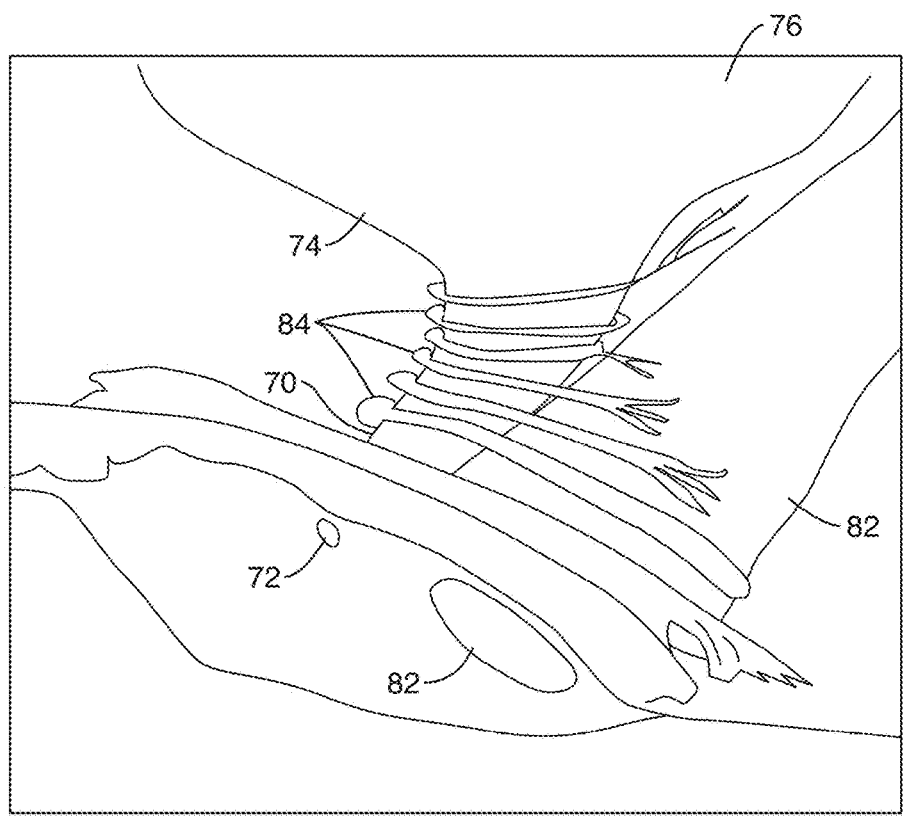
FIG. 7 is a perspective view of the bladder, urethra, and surrounding anatomy.

Referring to FIG. 7, the urethra 70 is surrounded along its length by the rhabdosphincter 84, a circular striated muscle that contracts to close the urethral lumen. The proximal ⅓ of sphincter, located toward proximal end 74 of the urethra, surrounds the urethra entirely. The middle ⅓ of the sphincter, located between proximal opening 74 and distal opening 72 of the urethra 70, surrounds the urethra 70 and is attached to the vaginal wall 82. The distal ⅓ of sphincter, located toward distal opening 72 of the urethra 70, surrounds both the urethra 70 and vagina 82.

Accordingly, treatment along the length of the urethra 70 will have varying efficacy depending on the location. In the cross-sectional view of the $50^{th}$ percentile of urethra 70 and surrounding anatomy shown in FIG. 7, the vaginolevator attachment 90, which in part comprises the periurethral ligament and paraurethral ligament, play a critical role in immobilization of the urethra 70 during increases in intra-abdominal pressure through lateral/posterior attachments to the levator ani muscles 86 and pelvic wall.

Figure 8:
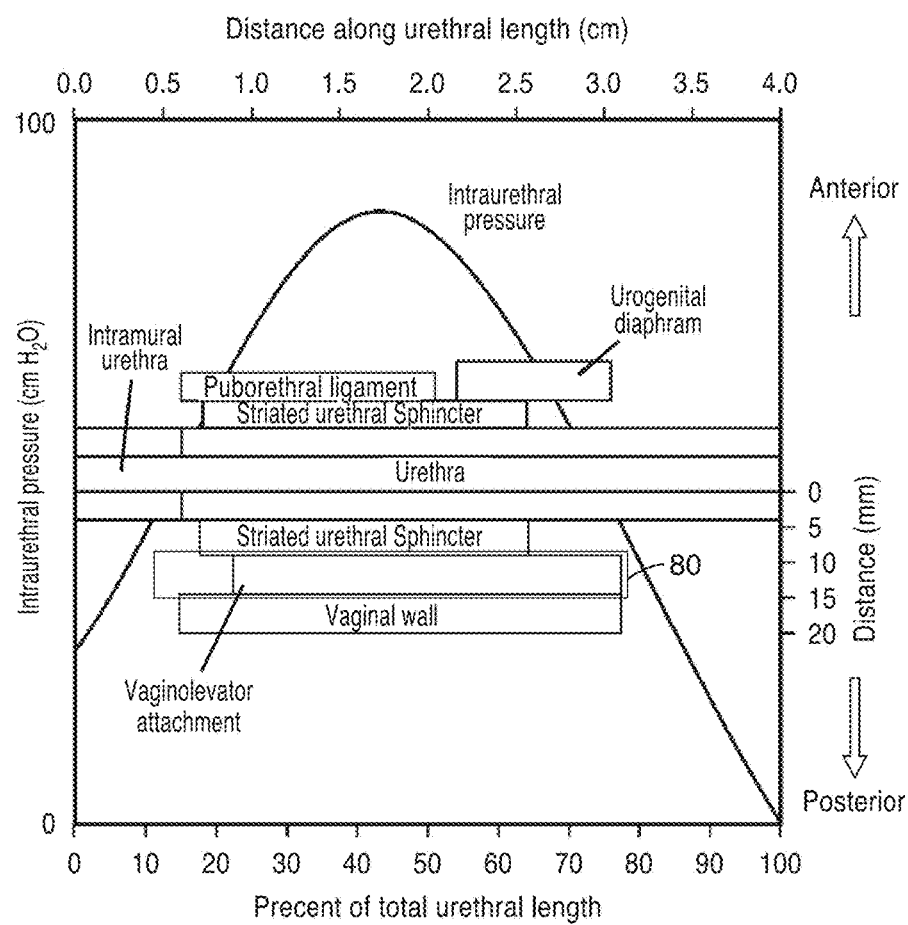
FIG. 8 is a graph showing anatomical landmarks of the pelvic anatomy as a function of distance and intraurethral pressure.

Referring to FIG. 8 and FIG. 9, the treatment region 80 most impacting for treating endopelvic fascia/vaginolevator attachment 90 for SUI is the mid-50% of urethral length, with insonation directed transurethrally toward vagina 82 with penetration of approximately 5-15 mm. The average thickness (lumen to exterior surface) of the urethral wall 70 and rhabdosphincter 84 is approximately 5 mm-7 mm. Reports of urethral wall thickness range from 1.5-11.0 mm, depending on age, degree of incontinence, measurement technique (e.g. transvaginal US, transurethral US, transrectal US, MRI, fixed tissue section) and position along wall 70. The urethral wall complex gets progressively thinner going anterior to lateral to posterior.

3. Transurethral Treatment Methods

FIG. 10A through FIG. 11 show embodiments of treatment devices configured for transurethral treatment of stress urinary incontinence by modeling/modification of specific anatomy illustrated in FIG. 5 though FIG. 9.

The methods illustrated in FIG. 10A through FIG. 11 are directed to an in-office, minimally invasive treatment for female stress urinary incontinence (SUI) due to urethral hypermobility. The treatment is generally configured to be performed in less than 30 minutes using local or oral sedation, has an excellent safety profile, and requires no hooks or incisions.

The treatment quality can be assessed using diagnostic ultrasound. The resulting therapy has durable outcomes lasting 2 years or more, with a 70% "cure" rate or better The methods of the technology described herein are preferably implemented with a small flexible catheter, such as catheters 10 and 50 shown in FIG. 1 through FIG. 4, which provide increased energy penetration in soft tissue to generate larger treatment volumes with shorter treatment times. 3-D control and directionality of ultrasound. The methods shown in 10A through FIG. 11 provide conformal treatment to target the shape/volume of the targeted tissue via dynamic control of energy during the procedure with custom/multiple delivery device configurations according to patient need, physician preference, etc.

In a preferred embodiment of the technology described herein (illustrated in FIG. 10A through FIG. 10C), the distal end 18 of the catheter 10 (with balloons 14 and 16 in a collapsed configuration) is inserted transurethrally at urethra entrance 72 such that distal end 18 extends into bladder 76 past proximal end 74 of urethra 70, until the transducers line up at the mid-50% of urethral length (FIG. 10B). The distal balloon 16 is then expanded to lock the location of the catheter 10 at the proximal opening 74 of the urethra 70, and the cooling balloon 14 is expanded while therapeutic ultrasound energy is delivered to target treatment region 80 (FIG. 10C).

In a preferred embodiment, the methods of the technology described herein are configured to denature collagen fibrils in endopelvic fascia to shrink and tighten during healing of the endopelvic fascia, and in particular the region of tissue referred to as the vaginolevator attachment 90 (see cross-sectional view of the urethra 70 and surrounding anatomy at the transducer 12 of inserted catheter 10, shown in FIG. 11). Accordingly, treatment is ideally directed within target treatment regions 80 within fascia 90.

While location of the tissue region 80 to be treated is paramount, the energy pattern is preferably directed so as not to modify or harm tissues that are sensitive to modification, e.g. nerve tissue, or the like. Branches of the pelvic and pudendal nerves 88 (see FIG. 11) enter the mid-urethra at 5 o'clock and 7 o'clock (with 12 o'clock anterior). These nerves control voluntary contraction of the external urethral sphincter Additional nerve bundles are identified in the posterior urethra, and 10 mm lateral in the fibromuscular tissue between urethra 70 and vagina 82. Proximally, scattered small ganglia and small unmyelinated nerves in predominately longitudinal orientation within loose areolar connective tissue. Smaller twigs present in smooth muscle walls of the vagina 82 and urethra 70. More distally, nerve fibers are reduced in number and size For the multi-sectored transducer configuration 12 illustrated in FIG. 4, a sizable dead zone 36 between sectors (≥60°) could be formed and aimed posterior toward vagina 82 to avoid damage to prominent neural bundles 88 between 5 and 7 o'clock between the urethra 70 and vagina 82.

90°-120° active sectors 34 may be aimed posterolateral at attachment 90 for generating spaced-apart treatment zones 80 that "straddle" the tissue occupied by nerve bundles 88, and other sensitive tissues. While the anatomy in FIG. 11 is shown symmetric about the sagittal plane, it is appreciated that patient anatomy may vary, and thus dead zone 36 and active sectors 34 may vary.

In one embodiment, the transducer 12 is positioned in mid-urethra 70, aimed posterolateral with 2×90°-100° tubular sectors 34 spaced apart by a dead zone 36 of approximately 60.

In one embodiment, an 80° acoustic dead zone 36 is located between active sectors 34 to limit nerve 88 temperature <45° C. This acoustic dead zone size can be achieved by making a 45° physical inactive zone. Given possible deviations in nerve location or mis-alignment of the device 10/50 within the urethra 70, safety may dictate a design closer to 60° physical inactive zone.

In another embodiment, the transducer 12 is positioned in mid urethra 70, aimed posterolateral with three treatment sectors 34 straddling 2 dead zone sectors 36 (e.g. three 80° treatment sectors 34, or two lateral 90° sectors and one posterior 60° sector, as shown in FIG. 22B).

In another embodiment (not shown) the transducer may be positioned in mid-urethra, aimed posterolateral with two 2×3.5 mm planar or curvilinear sectors or transducer segments The frequency at which the transducers 12 are operated is ideally selected (e.g. with controller 42 of FIG. 1) to generate a heating zone 80 approximately 1 mm to 15 mm radially from the balloon 14 or coupling structure.

While catheter 10 is primarily described above in the various embodiments, it is appreciated that the catheter 50 configuration may be applied similarly.

In an alternative embodiment shown in FIG. 10D, the catheter 10/50 heats a partial annular ring of endopelvic fascia tissue below the bladder neck 74 along the urethra 70 at a radial distance of 3-10 mm, to a temperature above 50° C. and below 75° C. for an appropriate number of seconds to produce collagen shortening and/or injury sufficient to stimulate healing response in target tissue 81. The peak temperature may be approximately 3-5 mm from the urethra surface, with cooler temperatures within tissues adjacent to the applicator cooling balloon. The diameter of the partial annular ring of heat (greater than 50° C.) preferably ranges from 10 mm to about 30 mm maximum. The urethra surface temperature can be regulated to be less than 45° C.

The urethra 70 surface temperature can be monitored with a thermocouple (not shown) to regulate applied power/coolant flow to balloon 14 to provide regulation. The applicator diameter can be 2-4 mm in diameter. The balloon can be 4-10 mm in diameter.

Application of ultrasound energy from within the urethra 70 to target tissue regions 80 can be used to generate tissue remodeling, stiffness changes, or desired tissue changes to treat SUI. The application of heat can be modulated or controlled (e.g. via controller 42) in temperature and duration for desired physiological effect. The application of ultrasound or acoustic energy can be controlled to produce heat therapy or for acoustic effects alone, or for targeted release of biologic agents or chemical agents, such as targeted microbubbles or nano-carriers, or acoustic or thermal release agents (not shown).

The device 10/50 may be scanned, sequentially rotated or translated to position and conform to the treatment or exposure area to a target 80.

Variable flow rates, temperature perfusate, liquids, and diameter shape balloons 14 can be used to cool or protect urethra 70 and extend therapy volume to outside or further into urethra 70 and surrounding tissue to protect urethra 70 and striated muscle 84 surrounding it. Device 10/50 may be increased in temperature or not circulated to bring treatment or therapy delivery to applicator boundary.

Further the coupling and cooling apparatus can be a rigid shell (non-collapsing) enclosing the coupling fluid and allowing temperature control.

Another embodiment is to position the ultrasound applicator in mid-urethra, and aim posterolateral with 2×100° tubular sectors one object.

Another embodiment is to position the ultrasound applicator in mid-urethra, and aim posterolateral with 2×3.5 mm planar sectors at another object.

The transurethral thermal treatment of connective tissue surrounding the urethra is directed to avoid thermal damage to nerve bundles critical to the ability of the urethral sphincter muscles to maintain continence. Transurethral thermal treatment of connective tissue surrounding the urethra is ideally directional to avoid thermal damage to the vaginal wall.

4. Experimental Results

FIG. 12A through FIG. 25 detail plots and images relating to simulation and experimental data with respect to the use of the devices of FIG. 1 through FIG. 4 and methods of FIG. 10A through FIG. 11 on tissue/simulated tissue corresponding to FIG. 5 though FIG. 9.

a. Biothermal Simulation

Figure 12A:
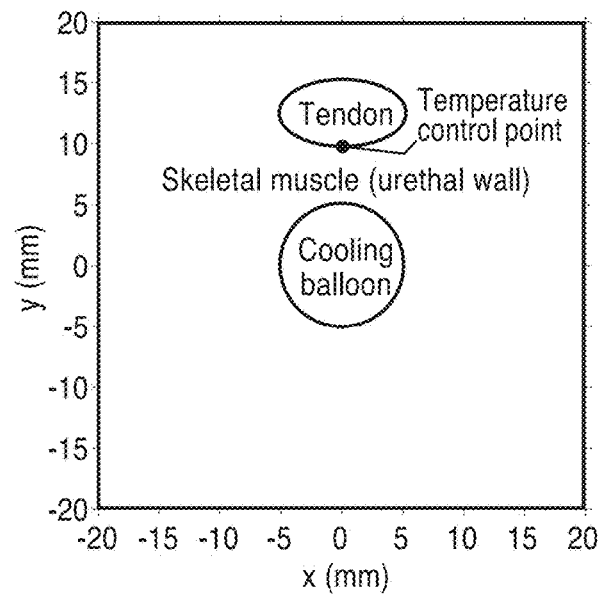
FIG. 12A shows a layout of the biothermal model with a tendon 5 mm from the cooling balloon.
Figure 12B:
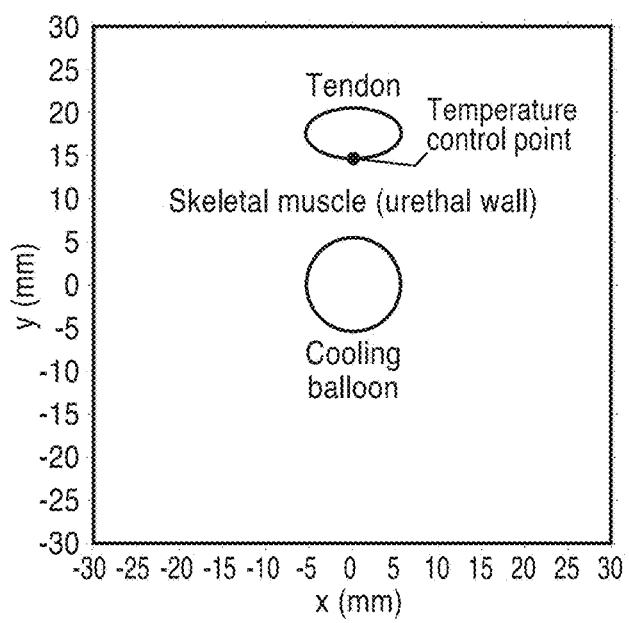
FIG. 12B shows a layout of the biothermal model with the tendon 10 mm from the balloon.

A 2-D, finite difference acoustic and biothermal model was used for generation of temperature distributions in representative urethral and periurethral tissue. The basic layout of the model is shown in FIG. 12A and FIG. 12B. FIG. 12A shows a layout of the biothermal model with a tendon (e.g. target treatment tissue) 5 mm from balloon 14. FIG. 12B shows a layout of the biothermal model with the tendon 10 mm from balloon 14. The ultrasound transducer 12 is located in the center of the cooling balloon 14. An ellipsoid of connective tissue (10 mm width×5 mm height) with properties similar to tendon is located at some distance from the cooling balloon. The intervening tissue is modeled as skeletal muscle representative of the urethral wall and associated musculature. The tendon is placed at 5 or 10 mm from the urethra to represent a range of urethral wall thickness based on observed values. These tissue types were given the acoustic and thermal properties shown in Table 2.

Three transducer shapes were modeled: planar (3.5×10 mm), curvilinear (3.5×10 mm, radius of curvature=15 mm), and tubular (3.5 mm OD, 90° active sector). Frequency was set to 3 or 6.5 MHz, temperature at the control point and the tendon was set to 50, 60, or 70° C. Table 3 shows the simulations performed using the various transducers.

The total simulation time was 15 minutes, comprised of 10 minutes of heating and 5 minutes of cool down. The steady-state temperature elevation was taken at 10 minutes. Dynamic changes in attenuation and perfusion values with heating were considered. A PID controller (e.g. controller 42 in FIG. 1) was used to ramp up power to achieve temperature elevation within 0.1° C. of the control point target temperature within 2 minutes. Cooling water flow at 25° C. and convective cooling coefficient h=1000 W/m$^2$-° C. was applied. Absorption was set equal to attenuation.

Table 4 shows the biothermal simulation results. FIG. 13A, FIG. 13B, and FIG. 13C show a plot of the results for tubular, planar, and curvilinear transducers, respectively, at $T_{control}$=60° C. and wall thickness of 5 mm. FIG. 14A, FIG. 14B, and FIG. 14C show a plot of the results for tubular, planar, and curvilinear transducers, respectively, for wall thickness of 5 mm at $T_{control}$=50° C.-70° C. FIG. 15A, FIG. 15B, and FIG. 15C show a plot of the results for tubular, planar, and curvilinear transducers, respectively, at $T_{control}$=60° C. and wall thickness of 10 mm.

In all cases, the maximum temperature was located within the connective tissue. The shape of the heating pattern varied with transducer shape and frequency. The 90° tubular transducer produced the widest heating zone, with the planar narrower and the curvilinear narrower still.

With the connective tissue at 5 mm, the 90° tubular, planar, and curvilinear devices have similar performance at 6.5 MHz. Lowering the frequency to 3 MHz for the planar device results in slightly less heating of urethral wall and increased heating of the connective tissue (higher Tmax, greater volume >60° C.). With the connective tissue at 10 mm, the planar and curvilinear devices produce a more desirable heating pattern than the tubular device in that temperature elevation is concentrated in the connective tissue with much less of the urethral wall above 50° C. Temperature elevation can be pushed into the connective tissue while reducing urethral wall heating by lowering the frequency from 6.5 MHz to 3 MHz.

FIG. 16A shows a plot of the radial distance from the balloon at 5 min with tendon at 5 mm. FIG. 16B shows a plot of the radial distance from balloon at 5 min with tendon at 10 mm.

With the connective tissue at 5 mm, the 90° tubular, planar, and curvilinear devices have similar performance at 6.5 MHz Lowering the frequency to 3 MHz for the planar results in slightly less heating of the urethral wall and increased heating of the connective tissue (higher Tmax, greater volume >60° C.). With the connective tissue at 10 mm, the planar and curvilinear devices produce a more desirable heating pattern than the tubular device in that temperature elevation is concentrated in the connective tissue with much less of the urethral wall above 50° C. Temperature elevation can be pushed into the connective tissue while reducing urethral wall heating by lowering the frequency from 6.5 MHz to 3 MHz.

FIG. 17A through FIG. 17F show a comparison of heating for the tubular, planar, and curvilinear devices operating at 6.5 MHz with connective tissue at 5 mm or 10 mm from the balloon surface. The target temperature for the PI controller is 60° C. at the interface of the urethral wall and connective tissue.

These plots suggest that 5-7.5 min heating duration does not provide a substantial benefit in heating of the connective tissue over a 1-2 min heating duration, and results in increased heating of the urethral wall tissue. An exception is the 90° tubular device treating connective tissue at 10 mm, where longer time duration is needed to extend heating to achieve the target temperature.

Heating was modeled with a 3.5×10 mm planar device aiming at a tendon in the configuration shown above. The tendon was placed at a distance of 5 mm or 10 mm from the 10 mm diameter cooling balloon containing the planar element. PI control was used to modulate power so that the temperature at the interface of the tendon and urethral wall is limited to 60° C. The transducer was operated over a frequency range from 3 MHz-7 MHz.

A comparison of the following parameters with frequency is made in Tables 5-7: radial location of the maximum temperature (r $T_{max}$), maximum temperature ($T_{max}$), radial dimension of the connective tissue heated to >55° C. (r tendon >55° C.), radial dimension of the connective tissue heated to >60° C. (r tendon >60° C.), radial location of the acoustic intensity peak (r $I_{max}$), and magnitude of the peak acoustic intensity ($I_{max}$).

The charts in FIGS. 18A and 18B show the maximum temperature and acoustic intensity with respect to frequency, respectively. The maximum temperature achieved within the connective tissue does not differ greatly over the 3-7 MHz frequency range. The acoustic intensity delivered to the connective tissue to achieve target temperature decreases with increasing frequency due to greater acoustic absorption at higher frequency.

FIGS. 19A and 19B illustrate differences in urethral wall heating and heating of the connective tissue over the frequency range radial plots.

b. Ex Vivo Analysis: Chicken Breast Experiment

A prototype transurethral device (TRUS1, e.g. catheter 50 of FIG. 3) was placed within chicken breast tissue, which represents the urethral wall composed of skeletal muscle.

The device 50 was aimed at tendon material embedded within the chicken breast, which represents periurethral tendons and endopelvic fascia. The tendon for the experimental model was extracted from cow foot. Tendons were placed at different distances from the device, and the device was operated under different power settings in an attempt to coagulate the tendon without coagulating the intervening chicken breast.

Beef tendon was embedded within chicken breast. Tendons were embedded at various distances (5, 7.5, 10, and 7.5 mm) from where the applicator will be placed.

The applicator was placed within chicken breast warmed in a 37° C. bath. Cooling flow was applied using room temperature water. The device was powered by an amplifier (Advanced Surgical Systems, Inc.) at 7.2 MHz.

The prototype device (e.g. similar to catheter 50 of FIG. 3) was configured with 2.5 mm OD transducer (9 mm balloon, 3 mm catheter) operated at 7.2 MHz peak driving frequency with efficiency=28%. Five heating trials were performed, as detailed below.

Trial 1: Tendon distance=5 mm; starting power=3.1 W; heating time=5 min; cooling time=3 min; water bath T=37.2° C., meat T=36.7° C. Result: It appeared that neither the chicken nor the tendon was coagulated.

Trial 2: Tendon distance=7.5 mm; starting power=6.1 W (measured 0.5 W reflected power); heating time=5 min; cooling time=3 min; water bath T=36.9° C., meat T=36.6° C., cooling water=21.5° C. Result: the chicken was coagulated but no obvious visual change was seen in the tendon.

Trial 3: Tendon distance=10 mm; starting power=5.1 W (measured 0.5 W reflected); heating time=5 min; cooling time=3 min; water bath T=37.1° C., meat T=36.9° C., cooling water=22.7° C. Result: again, chicken was visibly coagulated with no obvious visual change in the tendon.

Trial 4: Tendon at 7.5 mm; temperature probe embedded within tendon 1 mm from interface with chicken in direction of applicator; treatment goal: heat tendon to 60° C.; starting power=5.1 W; power increased to 6 W at 5 min, 7 W at 6 min, and 9 W at 8 min (1.3 W reflected power); total heating time=8.5 min; cooling was applied until the temperature was 42° C., at which point the device was removed. Cooling time=2.5 min. Result: again, coagulation was observed in the chicken but no visual change in the tendon.

Trial 5: Two tendons at 7.5 mm on either side of applicator. The active sector was aimed at one of the tendons with the other as a negative control; the temperature probe was embedded within heated tendon 1 mm from interface with chicken in the direction of the applicator; treatment goal was to heat tendon to 60° C., maintain for several minutes;

starting power=7.1 W; power increased to 9.1 W at 3 min; total heating time=6.5 min; tendon >60° C. for 2.5 min; cooling was applied until the temperature was 43° C., at which point the device was removed. Cooling time=3 min. Result: coagulation was observed in both the chicken and heated tendon. The chicken breast changed from dark pink to white while the tendon changed from white to translucent brown. This is noted in contrast to the unheated tendon, which remained white.

FIG. 20A-20B show plots results for the ex vivo experiment for temperature vs. time (FIG. 20A) and thermal dose (FIG. 20B).

In conclusion, the ability to coagulate tendon with exposure to 60° C. for >2 min was confirmed, although concomitant to coagulation of chicken breast. Heating the tendon without coagulating the chicken breast may require more careful power selection and possibly a lower frequency device or curvilinear device that focuses energy at a distance. Increased cooling by higher cooling flow or decreased cooling water temperature may be used to protect chicken breast from coagulation.

c. Heating Pattern Simulation and Analysis

FIG. 21A through FIG. 21 C show heating isotherms (from 45° C. to 60° C.), with the 30° lines representing the locations of nerve anatomy.

FIG. 21A shows the heating pattern isotherms for a dual-sectored transducer 12 having a 60° posterior dead zone. As can be seen, some heating in the 45° C. and 50° C. anatomy crosses the nerve locations, yet high temperatures above 55° C. remain directed toward the target anatomy.

FIG. 21B shows the heating pattern isotherms for a dual-sectored transducer 12 having an 80° posterior dead zone. The 45° C. isotherm approaches or touches the nerve locations, yet temperatures above 45° C. remain directed toward the target anatomy.

FIG. 21C shows the heating pattern isotherms for a dual-sectored transducer 12 having a 100° posterior dead zone. All isotherms are well separated from the nerve locations.

Referring to FIG. 22A through FIG. 25, an FEM solution was applied the bio-heat transfer equation (BHTE) for the applicators of the technology described herein as applied to the transurethral locations above to a simulated the target tissue model. Variable thermal and acoustic properties were applied for each tissue type. A complex US beam pattern model (rectangular radiator full-field, 1/r approximation) was modeled, along with dynamic changes to blood flow and attenuation with temperature.

Multi-sector control (dual sector and triple sector sonication) transducers were modeled having 10 mm & 15 mm lengths, with a 7 mm OD by×30 mm long cooling balloon. The applied intensity was between 14.5 W/cm$^2$-28 W/cm$^2$, with 1-5 min sonication.

FIG. 22A shows an image for simulation of dual-sector, lateral 90 degree sonication.

FIG. 22B shows an image for simulation of wide-angle triple-sector lateral 90 degree and posterior 60 degree sonication.

FIG. 23A shows an image for simulation of a 52° C. temperature/dose cloud at 3 min for simulation of a dual-sector dosing of FIG. 22A.

FIG. 23B shows an image for a simulation of a 52° C. temperature/dose cloud at 5 min for dual sector dosing of FIG. 22A.

FIG. 24A shows an image for a simulation of a 52° C. temperature/dose cloud at 1 min for the wide-angle triple-sector dosing of FIG. 22B.

FIG. 24B shows an image for a simulation of a 52° C. temperature/dose cloud at 2 min for the wide-angle triple-sector dosing of FIG. 22B.

FIG. 25 shows an image for a simulation of 52° C. temperature/dose clouds for the dual-sector dosing of FIG. 22A at 14.5 W/cm$^2$ for 10 mm and 15 mm transducers.

Embodiments of the technology described herein may be described with reference to flowchart illustrations of methods and systems according to embodiments of the technology described herein, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the technology described herein can be embodied in various ways, including the following:

1. An apparatus for treating stress urinary incontinence (SUI) by targeting a treatment region external to the urethra with ultrasound, the apparatus comprising: an elongate body comprising at least one lumen spanning from a proximal end of the elongate body to a distal end of the elongate body; at least one ultrasound transducer disposed on the elongate body near the distal end; wherein the at least one ultrasound transducer is configured to generate an ultrasound energy pattern having an inactive region disposed between a spaced apart active target treatments region; and wherein the at least one ultrasound transducer is configured to emit ultrasound treatment energy into the spaced apart active target treatments region corresponding to tissue external to the urethra, while not delivering ultrasound treatment energy to the inactive region to protect non-target anatomy from the emitted ultrasound energy.

2. The apparatus of any previous embodiment: wherein the at least one ultrasound transducer comprises a cylindrical transducer that is radially sectored to have at least two active sectors and at least one inactive sector; and wherein the at least two active sectors are configured to emit directed ultrasound energy into the spaced apart active target treatments region while not delivering ultrasound treatment energy from the inactive sector to protect non-target anatomy from the emitted ultrasound energy.

3. The apparatus of any previous embodiment, wherein the at least two active sectors are sized to direct delivery on target tissue comprising endopelvic fascia, supporting musculature, or associated connective tissue at a target location spaced apart from the urethra.

4. The apparatus of any previous embodiment, wherein the target tissue comprises a vaginolevator attachment.

5. The apparatus of any previous embodiment, wherein the at least one transducer is configured to deliver sufficient energy to remodel the target tissue to modify the stiffness of the target tissue.

6. The apparatus of any previous embodiment, wherein the inactive sector comprises a radial sector spanning at least 60 degrees.

7. The apparatus of any previous embodiment, wherein the spaced apart active target treatment region comprises two spaced apart active target treatment regions that straddle the inactive region.

8. The apparatus of any previous embodiment, wherein the at least two active sectors comprise radial sectors spanning at least 60 degrees.

9. The apparatus of any previous embodiment, further comprising: a cooling balloon disposed around a portion of the elongate body to enclose the at least one ultrasound transducer; the cooling balloon in fluid communication with the at least one lumen to allow delivery of a cooling fluid to the balloon.

10. The apparatus of any previous embodiment: wherein the cooling balloon has a collapsed configuration sized allow the distal end of the elongate body to be received within the urethra of a patient and delivered to a location within the urethra; and wherein the cooling balloon is configured to receive the cooling fluid to the cooling balloon to expand the cooling balloon against the urethra to provide cooling to urethral tissue in contact with the balloon.

11. The apparatus of any previous embodiment, further comprising: an anchoring balloon distal to said at least one transducer; wherein the anchoring balloon is configured to be expanded at a location within the bladder to position the at least one transducer adjacent the target region of tissue.

12. A method for treating stress urinary incontinence (SUI) by targeting treatment region external to the urethra with ultrasound, the method comprising: inserting an ultrasound therapy device into the urethra of a patient; advancing the ultrasound therapy device to a treatment location within the urethra; and emitting transurethral ultrasound energy from the treatment location to a target treatment region external to the urethra; wherein the target treatment region comprises endopelvic fascia, surrounding musculature, or associated connective tissue; and wherein the transurethral ultrasound energy comprises a directed energy pattern configured to remodel at least a portion of the endopelvic fascia, surrounding musculature, or associated connective tissue to modify stiffness of the target tissue.

13. The method of any previous embodiment: wherein the directed energy pattern is delivered simultaneously to at least two spaced apart target treatments regions; and wherein the two spaced apart target treatments regions straddle an inactive region substantially void of ultrasound energy emission.

14. The method of any previous embodiment, wherein emitting transurethral ultrasound energy comprises: emitting a directed energy pattern into a first active treatment region; rotating the ultrasound therapy device through an inactive treatment region; and emitting a directed energy pattern into a second active treatment region; wherein the first active treatment region is spaced apart from the first active treatment by the inactive treatment region.

15. The method of any previous embodiment, wherein the directed energy pattern comprises a sectored radial pattern having at least one active sector directed at the target treatment region and at least one inactive sector free from ultrasound treatment energy emission to protect non-target anatomy from the emitted ultrasound energy.

16. The method of any previous embodiment, wherein the target tissue comprises a vaginolevator attachment.

17. The method of any previous embodiment, wherein the at least one inactive sector comprises a radial sector spanning at least 60 degrees.

18. The method of any previous embodiment, wherein emitting transurethral ultrasound energy comprises emitting energy simultaneously to two active sectors spaced that are apart by the inactive sector to straddle the inactive sector.

19. The method of any previous embodiment, wherein the two active sectors comprise radial sectors spanning at least 60 degrees and the at least one inactive sector comprises a radial sector spanning at least 60 degrees.

20. The method of any previous embodiment, wherein the at least one inactive sector is configured to be directed posteriorly to protect at least one pelvic nerve bundle or vaginal wall associated with the urethra.

21. The method of any previous embodiment, further comprising: directing cooling fluid to the cooling balloon located at the treatment location: expanding the cooling balloon against the urethra; and cooling urethral tissue in contact with the balloon.

22. The method of any previous embodiment, further comprising: positioning an anchoring a balloon on a distal end of the therapy device at a location in the bladder of the patient; and expanding the anchoring balloon at the location within the bladder to position the therapy device at the target location within the urethra.

23. A method for transurethral treatment of stress urinary incontinence (SUI), comprising: inserting an ultrasound therapy device into the urethra of a patient; advancing the ultrasound therapy device to a treatment location within the urethra; and emitting transurethral ultrasound energy in a directed energy pattern from the treatment location to a target treatment region external to the urethra; wherein the directed energy pattern comprises a sectored radial pattern having at least one active sector directed on the target treatment region and at least one inactive sector free from ultrasound treatment energy emission to protect non-target anatomy from the emitted ultrasound energy.

24. The method of any previous embodiment: wherein the target treatment region comprises endopelvic fascia; and wherein the transurethral ultrasound energy comprises a directed energy pattern configured to remodel at least a portion of the endopelvic fascia to modify the stiffness of the target tissue.

25. The method of any previous embodiment, wherein the target tissue comprises a vaginolevator attachment.

26. The method of any previous embodiment, wherein the at least one inactive sector comprises a radial sector spanning at least 60 degrees.

27. The method of any previous embodiment, emitting transurethral ultrasound energy comprises emitting energy simultaneously to two active sectors spaced that are apart by the inactive sector to straddle the inactive sector.

28. The method of any previous embodiment, wherein the two active sectors comprise radial sectors spanning at least 60 degrees and the at least one inactive sector comprises a radial sector spanning at least 60 degrees.

29. The method of any previous embodiment, wherein the at least one inactive sector is configured to protect at least one pelvic nerve bundle or vaginal wall associated with the urethra.

30. The method of any previous embodiment, further comprising: directing cooling fluid to a cooling balloon located at the treatment location: expanding the cooling balloon against the urethra; and cooling urethral tissue in contact with the balloon.

31. The method of any previous embodiment, further comprising: positioning an anchoring a balloon on a distal end of the therapy device at a location in the bladder of the patient; and expanding the anchoring balloon at the location within the bladder to position the therapy device at the target location within the urethra.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Device | Transducer OD (mm) | Frequency (MHz) | Balloon OD (mm) | Catheter OD (mm) |
|---|---|---|---|---|
| TRUS1 | 2.5 | 7.4 | 9 | 2.8 |
| TRUS2 | 3.5 | 6.4 | 10 | 4 |

TABLE 2

| Tissue type | Thermal conductivity W/m-° C. | Density kg/m$^3$ | Heat capacity J/kg-° C. | Attenuation Np/m-MHz | Perfusion kg/m$^3$-s |
|---|---|---|---|---|---|
| Urethra | 0.5 | 1041 | 3810 | 5.7 | 0.7 |
| Tendon | 0.6 | 1130 | 3250 | 57.5 | 0.1 |

TABLE 3

| Transducer shape | Frequency | Target temp | Tendon distance |
|---|---|---|---|
| Planar | 3, 6.5 MHz | 50, 60, 70° C. | 5 mm |
| Planar | 6.5 MHz | 50, 60° C. | 10 mm |
| Curvilinear | 3, 6.5 MHz | 50, 60, 70° C. | 5 mm |
| Curvilinear | 6.5 MHz | 50, 60° C. | 10 mm |
| 90° tubular | 6.5 MHz | 50, 60, 70° C. | 5 mm |
| 90° tubular | 6.5 MHz | 50, 60° C. | 10 mm |

TABLE 4

| Urethral wall (mm) | Transducer shape | Freq (MHz) | $T_{control}$ (° C.) | r $T_{max}$ (mm) | $T_{max}$ (° C.) |
|---|---|---|---|---|---|
| 5 | Tub, 90° | 6.5 | 50 | 11.0 | 51.0 |
| 5 | Tub, 90° | 6.5 | 60 | 10.8 | 61.0 |
| 5 | Tub, 90° | 6.5 | 70 | 10.7 | 70.9 |
| 5 | Planar | 3.0 | 50 | 12.0 | 52.9 |
| 5 | Planar | 3.0 | 60 | 11.9 | 63.5 |
| 5 | Planar | 3.0 | 70 | 10.9 | 71.7 |
| 5 | Planar | 6.5 | 50 | 11.2 | 51.2 |
| 5 | Planar | 6.5 | 60 | 11.0 | 61.6 |
| 5 | Planar | 6.5 | 70 | 10.9 | 71.7 |
| 5 | Curvilinear | 3.0 | 50 | 12.9 | 54.5 |
| 5 | Curvilinear | 3.0 | 60 | 12.8 | 66.4 |
| 5 | Curvilinear | 3.0 | 70 | 12.8 | 78.2 |
| 5 | Curvilinear | 6.5 | 50 | 11.6 | 52.0 |
| 5 | Curvilinear | 6.5 | 60 | 11.2 | 63.2 |
| 5 | Curvilinear | 6.5 | 70 | 11.3 | 72.9 |
| 10 | Tub, 90° | 6.5 | 50 | 15.6 | 50.2 |
| 10 | Tub, 90° | 6.5 | 60 | 15.2 | 60.1 |
| 10 | Planar | 6.5 | 50 | 15.8 | 50.3 |
| 10 | Planar | 6.5 | 60 | 15.5 | 60.1 |
| 10 | Curvilinear | 6.5 | 50 | 15.7 | 50.3 |
| 10 | Curvilinear | 6.5 | 60 | 15.6 | 61.2 |

TABLE 5

| Tendon at 5 mm, Heating time = 1 min | | | | | | |
|---|---|---|---|---|---|---|
| Freq (MHz) | r $T_{max}$ (mm) | $T_{max}$ (mm) | r tendon >55° C. (mm) | r tendon >60° C. (mm) | r $I_{max}$ (mm) | $I_{max}$ (W cm$^{-2}$) |
| 3 | 6.4 | 62.7 | 4.4 | 3.0 | 5.1 | 1.03 |
| 4 | 6.2 | 62.0 | 3.9 | 2.4 | 5.1 | 0.88 |
| 5 | 6.0 | 61.5 | 3.5 | 2.0 | 5.1 | 0.79 |
| 6 | 5.8 | 61.1 | 3.1 | 1.6 | 5.1 | 0.72 |
| 7 | 5.7 | 60.8 | 2.8 | 1.3 | 5.1 | 0.67 |

TABLE 6

Tendon at 5 mm Heating time = 2 min

| Freq (MHz) | r $T_{max}$ (mm) | $T_{max}$ (mm) | r tendon >55° C. (mm) | r tendon >60° C. (mm) | r $I_{max}$ (mm) | $I_{max}$ (W cm$^{-2}$) |
|---|---|---|---|---|---|---|
| 3 | 6.6 | 63.0 | 4.9 | 3.4 | 5.1 | 0.92 |
| 4 | 6.3 | 62.3 | 4.4 | 2.8 | 5.1 | 0.78 |
| 5 | 6.1 | 61.7 | 4.0 | 2.3 | 5.1 | 0.70 |
| 6 | 5.9 | 61.3 | 3.6 | 1.9 | 5.1 | 0.64 |
| 7 | 5.8 | 61.0 | 3.3 | 1.6 | 5.1 | 0.59 |

TABLE 7

Tendon at 10 mm Heating time = 1 min

| Freq (MHz) | r $T_{max}$ (mm) | $T_{max}$ (mm) | r tendon >55° C. (mm) | r tendon >60° C. (mm) | r $I_{max}$ (mm) | $I_{max}$ (W cm$^{-2}$) |
|---|---|---|---|---|---|---|
| 3 | 11.3 | 61.7 | 4.1 | 2.6 | 10.1 | 0.85 |
| 4 | 11.0 | 61.1 | 3.6 | 2.0 | 10.1 | 0.72 |
| 5 | 10.8 | 60.7 | 3.2 | 1.5 | 10.1 | 0.63 |
| 6 | 10.6 | 60.4 | 2.9 | 1.1 | 10.1 | 0.57 |
| 7 | 10.5 | 60.1 | 2.6 | 0.8 | 10.1 | 0.52 |

TABLE 8

Tendon at 10 mm Heating time = 2 min

| Freq (MHz) | r $T_{max}$ (mm) | $T_{max}$ (mm) | r tendon >55° C. (mm) | r tendon >60° C. (mm) | r $I_{max}$ (mm) | $I_{max}$ (W cm$^{-2}$) |
|---|---|---|---|---|---|---|
| 3 | 11.2 | 61.4 | 4.5 | 2.5 | 10.1 | 0.70 |
| 4 | 11.0 | 60.9 | 3.9 | 1.9 | 10.1 | 0.58 |
| 5 | 10.7 | 60.6 | 3.5 | 1.4 | 10.1 | 0.51 |
| 6 | 10.6 | 60.3 | 3.1 | 1.0 | 10.1 | 0.45 |
| 7 | 10.4 | 60.1 | 2.8 | 0.7 | 10.1 | 0.40 |

What is claimed is:

1. A method for treating stress urinary incontinence (SUI) by targeting a treatment region external to the urethra with ultrasound, the method comprising:
   inserting an ultrasound therapy device into the urethra of a patient;
   advancing the ultrasound therapy device to a treatment location within the urethra; and
   emitting transurethral ultrasound energy from the treatment location to a target treatment region external to the urethra;
   wherein the target treatment region comprises a vaginolevator attachment in proximity to the urethra;
   wherein the transurethral ultrasound energy is emitted in a directed energy pattern focusing on and targeting the vaginolevator attachment, while excluding non-target tissue adjacent or in close proximity to the vaginolevator attachment; and
   as a result of the directed energy pattern, remodeling at least a portion of the target tissue region comprising collagen fibrils in the vaginolevator attachment to shrink and tighten the vaginolevator attachment.

2. A method as recited in claim 1:
   wherein the directed energy pattern is delivered simultaneously to at least two spaced apart target treatment regions; and
   wherein the two spaced apart target treatment regions straddle an inactive region substantially void of ultrasound energy emission, the inactive region corresponding to a location of the non-target tissue.

3. A method as recited in claim 1, wherein emitting transurethral ultrasound energy comprises:
   emitting a directed energy pattern into a first active treatment region;
   rotating the ultrasound therapy device through an inactive treatment region, the inactive region corresponding to a location of the non-target tissue; and
   emitting a directed energy pattern into a second active treatment region;
   wherein the first active treatment region is spaced apart from the second active treatment region by the inactive treatment region.

4. A method as recited in claim 1, wherein the directed energy pattern comprises a sectored radial pattern having at least one active sector directed at the target treatment region and at least one inactive sector free from ultrasound treatment energy emission to protect the non-target tissue from the emitted ultrasound energy.

5. A method as recited in claim 4, wherein the at least one inactive sector comprises a radial sector spanning at least 60 degrees.

6. A method as recited in claim 4, wherein emitting transurethral ultrasound energy comprises emitting energy simultaneously to two active sectors spaced that are apart by the inactive sector to straddle the inactive sector.

7. A method as recited in claim 6, wherein the two active sectors comprise radial sectors spanning at least 60 degrees and the at least one inactive sector comprises a radial sector spanning at least 60 degrees.

8. A method as recited in claim 4, wherein the at least one inactive sector is directed posteriorly to protect at least one pelvic nerve bundle or vaginal wall associated with the urethra.

9. A method as recited in claim 1, further comprising:
directing cooling fluid to a cooling balloon located at the treatment location;
expanding the cooling balloon against the urethra; and
cooling urethral tissue in contact with the balloon.

10. A method as recited in claim 9, further comprising:
positioning an anchoring balloon on a distal end of the therapy device at a location in the bladder of the patient; and
expanding the anchoring balloon at the location within the bladder to position the therapy device at the treatment location within the urethra.

11. A method as recited in claim 1, wherein the transurethral ultrasound energy is emitted in a radial energy pattern emanating from a mid-urethral location within the urethra.

12. A method as recited in claim 11, wherein the mid-urethral location is located between 5 and 15 mm from a proximal opening of the urethra.

13. A method as recited in claim 11, wherein the mid-urethral location is located at a mid-50% urethral length between a distal opening of the urethra and a proximal opening of the urethra at the bladder.

14. A method for transurethral treatment of stress urinary incontinence (SUI), comprising:
inserting an ultrasound therapy device into the urethra of a patient;
advancing the ultrasound therapy device to a treatment location within the urethra; and
emitting transurethral ultrasound energy in a directed energy pattern radially outward from the treatment location within the urethra to a target treatment region external to the urethra while excluding non-target tissue adjacent or in close proximity to the target treatment region;
wherein the directed energy pattern comprises a sectored radial pattern having at least one active sector directed on the target treatment region and at least one inactive sector free from ultrasound treatment energy emission to protect the non-target tissue from the emitted ultrasound energy;
wherein the target treatment region comprises a vaginolevator attachment in proximity to the urethra; and
wherein a active sector is emitted in a directed energy pattern centered on and targeting the vaginolevator attachment, while excluding the non-target tissue adjacent or in close proximity to the vaginolevator attachment.

15. A method as recited in claim 14, wherein the at least one inactive sector comprises a radial sector spanning at least 60 degrees.

16. A method as recited in claim 14, wherein emitting transurethral ultrasound energy comprises emitting energy simultaneously to two active sectors spaced apart by the inactive sector to straddle the inactive sector, the inactive sector corresponding to a location of the non-target tissue.

17. A method as recited in claim 16, wherein the two active sectors comprise radial sectors spanning at least 60 degrees and the at least one inactive sector comprises a radial sector spanning at least 60 degrees.

18. A method as recited in claim 17, wherein the at least one inactive sector is directed to protect at least one pelvic nerve bundle or vaginal wall associated with the urethra.

19. A method as recited in claim 14, further comprising:
directing cooling fluid to a cooling balloon located at the treatment location:
expanding the cooling balloon against the urethra; and
cooling urethral tissue in contact with the balloon.

20. A method as recited in claim 14, further comprising:
positioning an anchoring balloon on a distal end of the therapy device at a location in the bladder of the patient; and
expanding the anchoring balloon at the location within the bladder to position the therapy device at the treatment location within the urethra.

21. A method as recited in claim 14, wherein the transurethral ultrasound energy is emitted in a radial energy pattern emanating from a mid-urethral location within the urethra.

22. A method as recited in claim 21, wherein the mid-urethral location is located between 5 and 15 mm from a proximal opening of the urethra.

23. A method as recited in claim 21, wherein the mid-urethral location is located at a mid-50% urethral length between a distal opening of the urethra and a proximal opening of the urethra at the bladder.

* * * * *